(12) United States Patent
Dudley et al.

(10) Patent No.: US 8,700,337 B2
(45) Date of Patent: Apr. 15, 2014

(54) METHOD AND SYSTEM FOR COMPUTING AND INTEGRATING GENETIC AND ENVIRONMENTAL HEALTH RISKS FOR A PERSONAL GENOME

(75) Inventors: Joel T. Dudley, San Jose, CA (US); Atul J. Butte, Stanford, CA (US); Alexander A. Morgan, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 85 days.

(21) Appl. No.: 13/279,643

(22) Filed: Oct. 24, 2011

(65) Prior Publication Data

US 2012/0101736 A1 Apr. 26, 2012

Related U.S. Application Data

(60) Provisional application No. 61/406,447, filed on Oct. 25, 2010.

(51) Int. Cl.
G06F 19/00 (2011.01)
G06F 15/00 (2006.01)
A61B 5/00 (2006.01)

(52) U.S. Cl.
USPC .................................. 702/19; 700/1; 600/300

(58) Field of Classification Search
None
See application file for complete search history.

(56) References Cited

PUBLICATIONS

Ashley et al. Clinical assessment incorporating a personal genome The Lancet vol. 375 pp. 1525-1535 and Supplementary webappendix pp. 1-20 (2010).*

Ashley; et al., "Clinical assessment incorporating a personal genome", Lancet (2010), 375(9725):1525-1535.
Capriotti; et al., "Predicting the insurgence of human genetic diseases associated to single point protein mutations with support vector machines and evolutionary information", Bioinformatics (2006), 22(22):2729-2734.
Jakobsdottir; et al., "Interpretation of Genetic Association Studies: Markers with Replicated Highly Significant Odds Ratios May Be Poor Classifiers", PLOS Genetics (2009), 5(2):e1000337, 8 pages.
Jegga; et al., "PolyDoms: a whole genome database for the identification of non-synonymous coding SNPs with the potential to impact disease", Nucleic, Acids Research (2007), 35:D700-D706.
Pushkarev; et al., "Single-molecule sequencing on an individual human genome", Nature Biotechnology (2009), 27 (9):847-852.
Klein; et al., "Integrating genotype and phenotype information: an overview of the PharmGKB project", The Pharmacogenomics Journal (2001), 1:167-170.
Tucker; et al., "Massively Parallel Sequencing: The Next Big Thing in Genetic Medicine", The American Journal of Human Genetics (2009), 85:142-154.
UKPMC Funders Group, "Genome-wide association study of 14,000 cases of seven common diseases and 3,000 shared controls", Nature (2007), 447(7145):661-678.

* cited by examiner

*Primary Examiner* — John S Brusca
(74) *Attorney, Agent, or Firm* — Bozicevic, Field & Francis LLP; Pamela J. Sherwood

(57) ABSTRACT

Methods and systems are provided for the computation and display of an individual's personalized health risk based on the genome sequence of the individual, known etiological interactions between diseases for which the individual is determined to have genetic risk factors, and environmental etiological factors associated with the same diseases that represent potentially modifiable disease risk modifiers.

16 Claims, 9 Drawing Sheets

METHOD AND SYSTEM FOR COMPUTING AND INTEGRATING GENETIC AND ENVIRONMENTAL HEALTH RISKS FOR A PERSONAL GENOME

BACKGROUND OF THE INVENTION

Technological advance has greatly reduced the cost of genetic information to the point where it is possible to contemplate individual genome sequencing. Coupled with the enormous increase in available genetic data, there has been an ongoing effort into the assessment of associations between human genetic variation, physiology, and disease risk. As an increasing number of individual genome sequences are made available, there can be an evaluation of the biological, population, medical, and physical data for association statistics. This pool of combined data may provide for further information on the kinds and levels of variation that exist generally throughout and between individual genomes.

Individual genome information has the potential for personal health benefits by providing the information content of a large number of individual genetic tests, which may predict risk for serious disease. The availability of such knowledge can be utilized in further testing, medical intervention, and long term surveillance for signs of disease development.

However, the explanatory power and path to clinical translation of risk estimates for common variants reported in genome-wide association studies remain unclear. Much of the reason lies in the presence of rare and structural genetic variation. With the availability of rapid an inexpensive sequencing of complete genomes, comprehensive genetic risk assessment and individualization of treatment might be possible. However, present analytical methods are insufficient to make genetic data accessible in a clinical context, and the clinical usefulness of these data for individual patients has not been formally assessed. The present invention addresses the integrated analysis of a complete human genome in a clinical context.

SUMMARY OF THE INVENTION

Methods and systems are provided for the computation and display of an individual's personalized health risk based on the individual genome sequence, known etiological interactions between diseases for which the individual is determined to have genetic risk factors, and environmental etiological factors associated with the same diseases that represent potentially modifiable disease risk modifiers. The analysis is performed with novel computational methods, and is optionally displayed with a visualization approach useful in the clinical interpretation of risk factors personalized for the individual.

In a first component of the invention, an etiology integration engine takes as input the genetic data from the genome of an individual, utilizing per-disease combined genetic risks. Using a knowledge base system, the etiology integration engine (i) makes etiological connections between diseases for which the individual has been determined to have a genetic risk and (ii) makes etiological connections between these diseases and environmental factors that are disease risk modifiers.

In a second component, using network visualization methods, relationships between components, e.g. the disease and environmental conditions involved in integrated genomic and etiological risks for an individual, are graphically displayed, to aid in the identification of such relationships.

The risk assessment of the invention is useful in guiding treatment and preventive care for a patient. In some embodiments of the invention an individual is provided with an output that comprises a risk assessment diagram. In some embodiments an individual is further provided with a personalized guide for prevention and/or treatment of the risks identified by the methods of the invention.

In other embodiments, kits are provided for assessing integrated genetic and etiological risk in a human individual, the kit comprising reagents for data input and analysis for the methods described herein.

The above summary is not intended to include all features and aspects of the present invention nor does it imply that the invention must include all features and aspects discussed in this summary.

All publications and patent applications mentioned in this specification are herein incorporated by reference to the same extent as if each individual publication or patent application was specifically and individually indicated to be incorporated by reference.

DEFINITIONS

Figure 1:
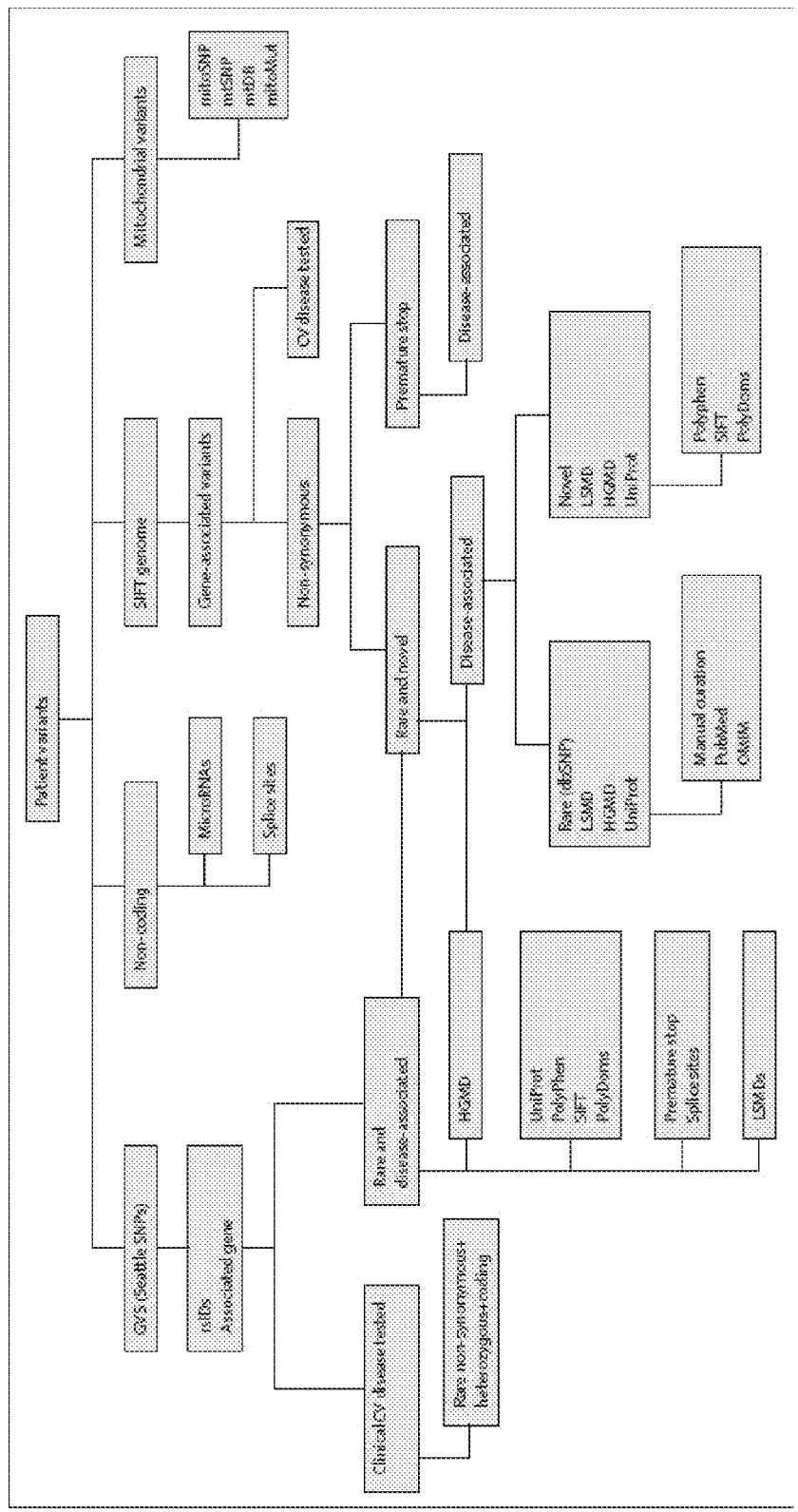
FIG. 1: Approach to rare or novel variants. CV=cardiovascular. GVS=Genome Variation Server. HGMD=Human Gene Mutation Database. LSMD=locus-specific mutation databases. mtSNP=human mitochondrial genome polymorphism database. OMIM=Online Mendelian Inheritance in Man. PolyDoms=mapping of human coding SNPs onto protein domains. PolyPhen=polymorphism phenotyping. rsID=reference sequence identification number. SIFT=Sorting Intolerant From Tolerant. SNP=single nucleotide polymorphism. UniProt=universal protein resource.

Genome Sequence Information.

As known in the art, the complete genome of an individual comprises the total chromosomal genetic sequence information. For the purposes of the present invention, the genome sequence information comprises all or a portion of the total genome sequence from the individual. In some embodiments the genome sequence information comprises the total non-redundant sequence of an individual genome. In other embodiments the genome sequence information comprises a dataset of single nucleotide polymorphisms (SNP) data from an individual obtained by sequencing or hybridization or a combination thereof, preferably by sequencing, e.g. at least about $10^5$ single nucleotide polymorphisms, usually at least about $5 \times 10^5$ SNPs, more usually at least about $10^6$ SNPs, and may be $2 \times 10^6$ SNPs or more. The genome sequence information may further comprise a dataset for copy number variations in the individual genome, e.g. at least about 100 copy number variations, at least about 200 copy number variations, at least about 500 copy number variations, or more.

Sequence analysis can also be used to detect specific polymorphisms in a nucleic acid. A test sample of DNA or RNA is obtained from the test individual. PCR or other appropriate methods can be used to amplify the gene or nucleic acid, and/or its flanking sequences, if desired. The sequence of a nucleic acid, or a fragment of the nucleic acid, or cDNA, or fragment of the cDNA, or mRNA, or fragment of the mRNA, is determined, using standard methods. The sequence of the nucleic acid, nucleic acid fragment, cDNA, cDNA fragment, mRNA, or mRNA fragment is compared with the known nucleic acid sequence of the gene or cDNA or mRNA, as appropriate.

Sequencing platforms that can be used in the present disclosure include but are not limited to: pyrosequencing, sequencing-by-synthesis, single-molecule sequencing, second-generation sequencing, nanopore sequencing, sequencing by ligation, or sequencing by hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437: 376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476, 504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

Allele-specific oligonucleotides can also be used to detect the presence of a polymorphism in a nucleic acid, through the use of dot-blot hybridization of amplified oligonucleotides with allele-specific oligonucleotide (ASO) probes (see, for example, Saiki, R. et al., Nature 324:163-166 (1986)). An "allele-specific oligonucleotide" (also referred to herein as an "allele-specific oligonucleotide probe") is an oligonucleotide of approximately 10-50 base pairs that specifically hybridizes to a nucleic acid, and that contains a polymorphism. An allele-specific oligonucleotide probe that is specific for particular polymorphisms in a nucleic acid can be prepared, using standard methods. With the addition of such analogs as locked nucleic acids (LNAs), the size of primers and probes can be reduced to as few as 8 bases.

In another aspect, arrays of oligonucleotide probes that are complementary to target nucleic acid sequence segments from an individual can be used to identify the presence of polymorphic alleles in a nucleic acid. For example, in one aspect, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092. These arrays can generally be produced using mechanical synthesis methods or light directed synthesis methods that incorporate a combination of photolithographic methods and solid phase oligonucleotide synthesis methods. See Fodor et al., Science 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings are incorporated by reference herein. Techniques for the synthesis of these arrays using mechanical synthesis methods are described in, e.g., U.S. Pat. No. 5,384,261; the entire teachings are incorporated by reference herein. In another example, linear arrays can be utilized.

Once an oligonucleotide array is prepared, a nucleic acid of interest is hybridized with the array and scanned for polymorphisms. Hybridization and scanning are generally carried out by methods described herein and also in, e.g., published PCT Application Nos. WO 92/10092 and WO 95/11995, and U.S. Pat. No. 5,424,186, the entire teachings are incorporated by reference herein. In brief, a target nucleic acid sequence that includes one or more previously identified polymorphic markers is amplified by well-known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Polymorphism, as used herein refers to variants in the gene sequence. Such variants may include single nucleotide polymorphisms, splice variants, insertions, deletions and transpositions. The polymorphisms can be those variations (DNA sequence differences) that are generally found between individuals or different ethnic groups and geographic locations which, while having a different sequence, produce functionally equivalent gene products. Polymorphisms also encompass variations which can be classified as alleles and/or mutations which can produce gene products which may have an altered function, i.e. variants in the sequence which can lead to gene products that are not functionally equivalent. Polymorphisms also encompass variations which can be classified as alleles and/or mutations which either produce no gene product, an inactive gene product or increased gene product. Further, the term is also used interchangeably with allele as appropriate.

Where a polymorphic site is a single nucleotide in length, the site is referred to as a single nucleotide polymorphism ("SNP"). SNP nomenclature used herein refers to the official Reference SNP (rs) ID identification tag as assigned to each unique SNP by the National Center for Biotechnological Information (NCBI), although other references may find use.

Risk Factor.

As used herein, a risk factor is a genetic or environmental exposure or characteristic, which, on the basis of epidemiologic evidence, is known to be associated with a health-related condition considered important to prevent. The term "risk factor", as described herein, means primarily increased susceptibility to a human disease, e.g. diabetes, cancer, cardiovascular disease, and the like. Thus, particular genetic variants or environmental exposures may be characteristic of increased susceptibility of disease, as characterized by a relative risk of greater than one.

Likelihood Ratio.

For genetic variants, e.g. SNP variants, copy number variants, etc., a likelihood ratio (LR) of disease risk may be calculated published information reporting association with disease, which association is optionally stratified by sex, ethnicity, age, etc. For each variant the LR may be calculated as the probability of the genotype appearing in a disease, or case population/probability of the genotype appearing in control population.

To calculate the likelihood ratio (LR), a genetic association database is utilized that provides case/control associations with diseases in a population of interest. For every disease SNP, we calculated the LR for each genotype using the following equation:

$$LR = \frac{\text{probability of the genotype in the control population}}{\text{probability of the genotype in the case population}}$$

Odds Ratio.

The odds ratio is a measure of effect size, describing the strength of association or non-independence between two binary data values. It is used as a descriptive statistic, and plays an important role in logistic regression. Unlike other measures of association for paired binary data such as the relative risk, the odds ratio treats the two variables being compared symmetrically, and can be estimated using some types of non-random samples.

The odds ratio is the ratio of the odds of an event occurring in one group to the odds of it occurring in another group. An odds ratio of 1 indicates that the condition or event under study is equally likely to occur in both groups. An odds ratio greater than 1 indicates that the condition or event is more likely to occur in the first group. And an odds ratio less than 1 indicates that the condition or event is less likely to occur in the first group. The odds ratio must be greater than or equal to zero if it is defined. In clinical studies the parameter of greatest interest is often the relative risk rather than the odds ratio. The relative risk is best estimated using a population sample, but if the rare disease assumption holds, the odds ratio is a good approximation to the relative risk—the odds is p/(1−p), so when p moves towards zero, 1−p moves towards 1, meaning that the odds approaches the risk, and the odds ratio approaches the relative risk.

A feature of the invention is the generation of a database of risk associations for a variety of genetic variants and environmental factors. Such a database will typically comprise associations as described above, for a number of variants and factors, which may be selected and arranged according to various criteria. The databases may be provided in a variety of media to facilitate their use. "Media" refers to a manufacture that contains the datasets of the present invention. The datasets can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

As used herein, the term "nucleic acid probe" refers to a molecule capable of sequence specific hybridization to a nucleic acid, and includes analogs of nucleic acids, as are known in the art, e.g. DNA, RNA, peptide nucleic acids, and the like, and may be double-stranded or single-stranded. Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

"Specific hybridization," as used herein, refers to the ability of a first nucleic acid to hybridize to a second nucleic acid in a manner such that the first nucleic acid does not hybridize to any nucleic acid other than to the second nucleic acid. "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 85%, 90%, 95%). The percent homology or identity of two nucleotide or amino acid sequences can be determined by aligning the sequences for optimal comparison purposes (e.g., gaps can be introduced in the sequence of a first sequence for optimal alignment). The nucleotides or amino acids at corresponding positions are then compared, and the percent identity between the two sequences is a function of the number of identical positions shared by the sequences (i.e., % identity=# of identical positions/total # of positions×100). When a position in one sequence is occupied by the same nucleotide or amino acid residue as the corresponding position in the other sequence, then the molecules are homologous at that position. As used herein, nucleic acid or amino acid "homology" is equivalent to nucleic acid or amino acid "identity". A preferred, non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., W=5 or W=20).

A "marker", as described herein, refers to a genomic sequence characteristic of a particular allele at a polymorphic site.

A "haplotype," as described herein, refers to a segment of a genomic DNA strand that is characterized by a specific combination of genetic markers ("alleles") arranged along the segment. In a certain embodiment, the haplotype can comprise one or more alleles, two or more alleles, three or more alleles, four or more alleles, or five or more alleles.

"Comparable cell" shall mean a cell whose type is identical to that of another cell to which it is compared. Examples of comparable cells are cells from the same cell line.

"Inhibiting" the onset of a disorder shall mean either lessening the likelihood of the disorder's onset, or preventing the onset of the disorder entirely. In the preferred embodiment, inhibiting the onset of a disorder means preventing its onset entirely.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

"Inhibiting" the expression of a gene in a cell shall mean either lessening the degree to which the gene is expressed, or preventing such expression entirely. "Specifically inhibit" the expression of a protein shall mean to inhibit that protein's expression (a) more than the expression of any other protein, or (b) more than the expression of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present application may make reference to information provided in Ashley et al. (2010) Lancet 375:1525-35, including supplemental materials provided therein, which is herein specifically incorporated by reference in its entirety.

DETAILED DESCRIPTION OF THE EMBODIMENTS

Methods of integrating genetic and environmental risk factors to provide a personalized overall risk assessment for an individual are provided herein. By evaluating an individual genotype for the presence of polymorphisms in relevant genes, integrated with environmental factors influencing the individual, the susceptibility to development of disease can be predicted. The knowledge about integrated risks allows for the ability to maintain specific testing and thus to diagnose the disease at an early stage, to provide information to the clinician about prognosis for disease in order to be able to apply the most appropriate treatment, to provide assessment for lifestyle changes commensurate with risk factors, and the like. In some embodiments of the invention an individual is provided with an output that comprises a risk assessment diagram. In some embodiments an individual is further provided with a personalized guide for prevention and/or treatment of the risks identified by the methods of the invention.

In some embodiments, the methods of the invention comprise inputting genome sequence information from an individual into an etiology integration engine to make connections between diseases for which the individual has been determined to have a genetic risk, and between these diseases and environmental factors that are disease risk modifiers. The genome sequence information comprises all or a portion of the total genome sequence from the individual. The genome sequence information may comprise the total sequence of an individual genome. Alternatively the input genome sequence information may comprise a set of SNP data, e.g. at least about $10^5$ SNPs, usually at least about $5 \times 10^5$ SNPs, and may be $10^6$ SNPs, $2 \times 10^6$ SNPs or more.

The genome sequence information is initially analyzed for variants in coding and non-coding regions, utilizing public databases of human genetic sequence information. Analysis is performed on four areas: (i) variants associated with genes for mendelian disease; (ii) novel mutations; (iii) variants known to modulate response to pharmacotherapy; and (iv) single nucleotide polymorphisms previously associated with complex disease.

The analysis includes a comparison with variants having validated reference SNPs, and an analysis for novel variants. Public databases of sequence information include, without limitation, dbSNP from the National Institutes of Health, the SNP consortium, European SNP database, and the human genome variation database. A comparison is made with the validated SNPs and the match data for the genome being analyzed is input to the etiology integration engine.

In some embodiments of the invention a high-quality disease-associated SNP database is utilized, where the database is built from the publicly available SNP information at dbSNP from those SNPs relevant to human disease. The database entries for each SNP may include, without limitation, a disease name, specific phenotype, study population, case and control population, genotyping technology, major/minor/risk alleles, likelihood ratio, likelihood ratio, odds ratio, 95% confidence interval of the odds ratio, published p-value, and genetic model for each included, statistically significant genotype comparison. Preferred information includes a disease name and odds ratio for the SNP. To enable the integration of multiple studies on similar diseases and phenotypes, the disease/phenotype names in our association database are mapped to the Unified Medical Language System (UMLS) Concept Unique Identifiers (CUIs). The SNP data may further be subjected to an algorithm to correctly identify the strand direction and suitably annotated.

The analysis of novel variants may utilize one or more independent analysis tools, usually two or more, three, four or more analysis tools. Tools include the (a) "Sorting Intolerant from Tolerant" (SIFT) algorithm, which predicts the effects of non-synonymous polymorphisms on protein function based on homology, conservation, and physical properties of amino acid substitutions; (b) the "Polymorphism Phenotyping" (PolyPhen) tool, which predicts the impact of amino acid changes on protein function using an algorithm that incorporates information on site of substitution, i.e., whether an amino acid change occurs in one of several sites of functional importance such as binding sites or trans-membrane regions, sequence alignment, and known protein structural changes; (c) query for rare coding variants using the Universal Protein Resource (UniProt) database consisting of annotated protein sequence variation data with experimentally proven or computer-predicted data to support phenotypic association; and analysis for coding region variants that produce premature stop codons or read-throughs in existing stop codons, e.g. using the PolyDoms database, which incorporates SNP-phenotype associations from several different sources, including SIFT, PolyPhen, Uniprot, Database of Secondary Structure in Proteins, Protein Databank, and Database of Secondary Structure in Proteins.

The genome sequence information is also analyzed for variants in on-coding regions, e.g. the SNP databases referenced above, and other public databases, which include without limitation, Online Mendelian Inheritance of Man; Human Gene Mutation Database; Pubmed, and the like.

The analysis of genetic information thus obtained provides an initial estimate of disease association between the genome information of the individual and known disease correlations. A likelihood ratio (LR) of disease risk is calculated for each SNP having a disease association. The pre-test probability for disease is calculated from the LR using criteria specific for the individual, which criteria may include, without limitation, age, sex, weight, ethnicity, and the like.

A post-test calculation of developing disease is then made. The post-test probability is calculated as follows. For SNPs with multiple LR from multiple studies, the mean LR is calculated, and weighted by the square root of sample sizes. The human genome is partitioned into Haplotype blocks, and for each haplotype block, the highest LR SNP is used. LR from all SNPs are multiplied to report the cumulative LR for the individual, and the cumulative LR calculated for all relevant diseases. The pre-test probability is translated into pretest odds, multiplied by the cumulative LR to get post-test odds, and then converted to the post-test probability using the following equations:

pre-test odds=pre-test probability/1−pre-test probability post-test odds=pre-test odds×LR pest-test probability=post-test odds/1+post-test odds As a second component of the risk integration analysis, gene-environment interaction and conditionally dependent risk are analyzed. A database of established links between diseases and known etiological factors is obtained by mapping Medical Subject Heading (MeSH) annotations in the MEDLINE database to the Unified Medical Language System (UMLS) semantic network, keeping only those publications with annotations representing diseases and environmental factors. A compilation of drug-related genotype-phenotype associations is then drawn from a public database, utilizing, for example, the Pharmacogenomics Knowledgebase.

An output of the combined risk factor thus obtained may be presented to the individual, including the post-test calculations of disease and environmental interactions. In a preferred embodiment, the information thus obtained is presented in a conditional dependency diagram for diseases represented in the patient's genetic-risk profile. Such a diagram may represent diseases having a significant post-test risk probability, e.g. 5%, 10%, 15%, etc., with connections between diseases if one disease predisposes a patient to the other. Environmental factors, e.g. those that are potentially modifiable may be presented, including showing an association between an environmental factor and a disease if there is a reported association.

In addition to distance and association visualization, the display of information may include other classification schemes to aid in analysis. Each point, which represents a disease in the analysis matrix, may be arbitrarily assigned features, such as color, size, shape, etc. where the assignment provides information about the condition. For example, the size of the point may represent the risk of disease; or may convey the seriousness of the disease. Colors and shapes may be used in various ways, e.g. to represent classes of diseases, compounds or environmental factors, such as steroids, lipids, polypeptides, polynucleotides, and the like; species of origin or gene families; signaling pathways; and the like.

Such additional information may also be conveyed by the use of multiple visualization windows. In addition to the graphic display of clustering information, the windows may contain text annotation of the profile; different spatial views of the matrix, different features, selected regions, and the like.

The risk analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes. Preferably, the invention is implemented in computer programs executing on programmable computers, comprising a processor, a data storage system (including volatile and nonvolatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

EXPERIMENTAL

The following methods were used in the examples that are described further below to illustrate embodiments of the present invention.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

The following examples are offered by way of illustration and not by way of limitation.

Example 1

Clinical Assessment Incorporating a Personal Genome

The cost of genomic information has fallen steeply, but the clinical translation of genetic risk estimates remains unclear. We aimed to undertake an integrated analysis of a complete human genome in a clinical context. We assessed a patient with a family history of vascular disease and early sudden death. Clinical assessment included analysis of this patient's full genome sequence, risk prediction for coronary artery disease, screening for causes of sudden cardiac death, and genetic counseling. Genetic analysis included the development of novel methods for the integration of whole genome and clinical risk. Disease and risk analysis focused on prediction of genetic risk of variants associated with mendelian disease, recognized drug responses, and pathogenicity for novel variants. We queried disease-specific mutation databases and pharmacogenomics databases to identify genes and mutations with known associations with disease and drug response. We estimated post-test probabilities of disease by applying likelihood ratios derived from integration of multiple common variants to age-appropriate and sex-appropriate pretest probabilities. We also accounted for gene-environment interactions and conditionally dependent risks.

Analysis of 2.6 million single nucleotide polymorphisms and 752 copy number variations showed increased genetic risk for myocardial infarction, type 2 diabetes, and some cancers. We discovered rare variants in three genes that are clinically associated with sudden cardiac death—TMEM43, DSP, and MYBPC3. A variant in LPA was consistent with a family history of coronary artery disease. The patient had a heterozygous null mutation in CYP2C19 suggesting probable clopidogrel resistance, several variants associated with a positive response to lipid-lowering therapy, and variants in CYP4F2 and VKORC1 that suggest he might have a low initial dosing requirement for warfarin. Many variants of uncertain importance were reported.

Our results show that whole-genome sequencing can yield useful and clinically relevant information for individual patients.

Methods

Patient.

A patient with a family history of vascular disease and early sudden death was assessed at Stanford's Center for Inherited Cardiovascular Disease by a cardiologist and a board-certified genetic counselor. We took the patient's medical history and he was clinically assessed. A four-generation pedigree was drawn. In view of his family history, he underwent electrocardiography, an echocardiogram, and a cardiopulmonary exercise test.

Genome Analysis.

Technical details of genome sequencing for this patient have been described previously. In brief, genomic DNA was purified from 2 mL of whole blood and sequenced with a Heliscope (Helicos BioSciences, Cambridge, Mass., USA) genome sequencer. We mapped sequence data to the National Center for Biotechnology Information reference human genome build 36 using the open-source aligner IndexDP (Helicos BioSciences, Cambridge, Mass., USA). Base calling was done with the UMKA algorithm. A subset of single nucleotide polymorphism calls were independently validated with the Illumina BeadArray (San Diego, Calif., USA) and all variants reported here and discussed with the patient were validated with Sanger sequencing. A subset of copy number variation calls were independently validated with digital PCR.

Disease and Risk Analysis.

Analysis focused on four areas: (i) variants associated with genes for mendelian disease; (ii) novel mutations; (iii) variants known to modulate response to pharmacotherapy; and (iv) single nucleotide polymorphisms previously associated with complex disease. Database queries, biophysical prediction algorithms, and analyses of non-coding regions were used to screen for rare and novel variants in the genome. We examined disease specific mutation databases, the human genome mutation database, and Online Mendelian Inheritance in Man to identify genes and mutations with known associations to monogenic diseases. We applied prediction algorithms to weight the likelihood of variant pathogenicity on the basis of allele frequency, conservation, and protein domain disruption. Additionally, we developed algorithms to index variants affecting or creating start sites, stop sites, splice sites, and microRNAs (FIG. 1). The Pharmacogenomics Knowledge Base (PharmGKB) contains data for 2500 variants, of which 650 refer specifically to drug-response phenotypes. PharmGKB curators examined these 650 annotations in the context of the patient's genotype. Key variants were identified on the basis of the relevance of the phenotype in the annotation, the medical and family history, and the study population on which the annotation was based. Since our disease-risk estimation and pharmacogenomic analysis drew on previous reports, we rated the evidence used in one of three categories.

To integrate common variant genetic risk across a range of human disease, we built a manually curated disease and single-nucleotide-polymorphism database. Diseases and phenotypes were mapped to Unified Medical Language System Concept Unique Identifiers. Since strand direction was variably reported between studies, we identified strand direction by comparing with major or minor alleles in the appropriate HapMap population. Odds ratios were available for allele comparisons in most cases; however, to generate a medically relevant post-test probability of disease from integrated environmental and genetic risk, we calculated likelihood ratios (LRs) for the most important single nucleotide polymorphism from every haplotype block. Pre-test probability was derived from published sources and the LR was applied to the pre-test odds of disease, which were calculated from age appropriate and sex-appropriate population prevalence. Investigators did not always provide frequency data for genotype that allowed calculation of the LR. The study was reviewed by the institutional review board of Stanford University and the patient gave written consent. The patient received education and counseling before signing the consent form and throughout testing and follow-up.

Results

The patient was a 40-year-old man who presented with a family history of coronary artery disease and sudden death. His medical history was not clinically significant and the patient exercised regularly without symptoms. He was taking no prescribed medications and appeared well. Clinical characteristics were within normal limits (table 1). Electrocardiography showed sinus rhythm, normal axis, and high praecordial voltage with early repolarisation. An echocardiogram revealed normal right and left ventricular size, systolic, diastolic, and valvular function. There were no wall motion abnormalities during maximum exercise and 1-5 mm ST depression was upsloping. Maximum oxygen uptake was 50 mL/kg per min. A four-generation family pedigree (FIG. 2) showed atherosclerotic vascular disease with several manifestations and prominent osteoarthritis. The patient's first cousin once removed (IV-1) died suddenly of an unknown cause.

TABLE 1

Clinical characteristics of the patient

|  | Patient | Reference range |
|---|---|---|
| Age (years) | 40 | — |
| Height (cm) | 180 | — |
| Weight (kg) | 86 | — |
| Body-mass index (kg/m$^2$) | 26.5 | — |
| Blood pressure |  | — |
| Systolic (mmHg) | 128 | — |
| Diastolic (mmHg) | 80 | — |
| Laboratory testing |  |  |
| Haemoglobin (mmol/L) | 9.7 | 8.4-11.0 |
| Creatinine (μmol/L) | 106.1 | <110 |
| Urea nitrogen (mmol/L) | 7.1 | 1.8-8.9 |
| Leucocyte count (10$^3$ per μL) | 4.9 | 4-11 |
| Cholesterol |  |  |
| Total (mmol/L) | 5.6 | — |
| LDL (mmol/L) | 4.0 | — |
| HDL(mmol/L) | 1.2 | — |
| Triglycerides (mmol/L) | 0.8 | — |
| High-sensitivity C-reactive protein (nmol/L) | <2 | <25 |
| Lipoprotein(a) (nmol/L) | 285 | <75 |
| Exercise testing |  |  |
| MaximumVO$_2$ (mL/kg per min) | 49.6 | — |
| Maximum external work (W) | 450 | — |
| Ve/VCO$_2$ slope | 26 | — |
| Maximum heart rate (bpm) | 191 | — |
| Resting cardiac output (L/min) | 6.3 | — |
| Maximum cardiac output (L/min) | 24.5 | — |
| Electrocardiography |  |  |
| Heart rate (bpm) | 60 | — |
| QTc (ms) | 421 | — |
| Echocardiography |  |  |
| Interventricular septum diastole (mm) | 10 | 6-11 |
| Left ventricular posteriorwall diastole (mm) | 9.7 | 6-11 |

TABLE 1-continued

Clinical characteristics of the patient

|  | Patient | Reference range |
|---|---|---|
| Left ventricular internal diameter diastole (mm) | 45 | 37-57 |
| Ejection fraction by method of discs (%) | 63% | >55% |
| Aortic root diameter (mm) | 36 | 25-40 |
| Mitral inflow |  |  |
| E (cm/s) | 84 | — |
| a (cm/s) | 53 | — | bpm = beats per minute.
E = early diastolic peak velocity.
a = late diastolic peak velocity due to a trial contraction.

Sequencing of genomic DNA resulted in an output of 148 GB of raw sequence, with an average read length of 33 bases. Base calling detected 2.6 million single nucleotide polymorphisms and 752 copy number variations. An important benefit of sequencing compared with DNA chip-based methods of genotyping is the identification of rare or novel variants. We searched for evidence of rare or novel variants that would predispose the patient or his family to disease. Specific to cardiovascular disease, we discovered rare variants in three genes that are clinically associated with sudden cardiac death—TMEM43, DSP, and MYBPC3. The MYBPC3 variant, encoding an arginine-to-glutamine change at position 326 of the cardiac myosin-binding protein C, was originally associated with late-onset hypertrophic cardiomyopathy. Subsequently, this variant has also been reported in several independent control populations without known hypertrophic cardiomyopathy, suggesting that it might be benign. Mutations in TMEM4330 or DSP31 have been associated with familial arrhythmogenic right-ventricular dysplasia or cardiomyopathy. Review of previous clinical assessment of extended family members revealed minor criteria for this disease in one first cousin, whose son died suddenly in his teens. By contrast with the findings for the identified rare MYBPC3 variant, the TMEM43 variant, encoding a methionine-to-valine change at position 41 of transmembrane protein 43, has not been previously published, but was seen in one of 150 probands with arrhythmogenic right-ventricular dysplasia or cardiomyopathy. The identified DSP variant, encoding an arginine-to-histidine change to aminoacid 1838 of the desmoplakin protein, is entirely novel. Control populations from clinical testing laboratories (more than 1000 total chromosomes) did not contain either the DSP or TMEM43 variants.

TABLE 2

Selected rare non-synonymous variants in genes associated with inherited disease

| Gene | Amino-acid substitution | Gene name | Chromosome number | Position | SNP location | Reference base* |
|---|---|---|---|---|---|---|
| Previously described rare variants in genes associated with common disease | | | | | | |
| LPA[15,16] | I4399M¶ | Apolipoprotein A precursor, lipoprotein(a) | 6 | 160881127 | rs3798220 | T |
| FRZB[17] | R200W | Frizzled-related protein | 2 | 183411581 | rs288326 | G |
| Previously described rare variants in genes associated with rare disease | | | | | | |
| HFE | H63D | Hereditary haemochromatosis protein precursor | 6 | 26199158 | rs1799945 | C |
| BTD[20] | D444H | Biotinidase precursor | 3 | 15661697 | rs13078881 | G |
| SLC26A2[21] | R492W | Solute carrier family 26 (sulphate transporter), member 2 | 5 | 149340823 | None | C |

TABLE 2-continued

Selected rare non-synonymous variants in genes associated with inherited disease

| Gene | Variant | Protein | Chr | Position | dbSNP | Allele* |
|---|---|---|---|---|---|---|
| LAMB3[22] | R635X | Laminin, β3 | 1 | 207865689 | None | G |
| SLC3A1[23] | M467T | Solute carrier family 3 (cystine, dibasic, and neutral aminoacid transporters) member 1 | 2 | 44393296 | None | T |
| *Previously described variants of unknown importance in disease-associated genes* | | | | | | |
| TMEM43[24] | M41V | Transmembrane protein 43 | 3 | 14146021 | None | A |
| MYBPC3[25] | R326Q | Myosin-binding protein C, cardiac-type | 11 | 47324447 | rs34580776 | C |
| *Novel variants potentially associated with rare disease* | | | | | | |
| DSP[11] | R1838H | Desmoplakin | 6 | 7528007 | Novel | G |
| CDC73[26] | Q430X | Parafibromin | 1 | 191468879 | Novel | C |
| CFTR[27] | G458R | Cystic fibrosis transmembrane conductance regulator | 7 | 116976093 | Novel | G |
| HFE2 | H174Y | Haemojuvelin precursor | 1 | 144127058 | Novel | C |

| | Patient genotype | Associated disease † | Mutation database‡ | Functional prediction§ | Mode of disease-gene inheritance |
|---|---|---|---|---|---|
| *Previously described rare variants in genes associated with common disease* | | | | | |
| LPA[15,16] | C/T | Coronary artery disease | Associated with high lipoprotein(a) concentrations | Benign | NA |
| FRZB[17] | A/G | Osteoarthritis | Possibly associated with osteoarthritis\|\| | Damaging | NA |
| *Previously described rare variants in genes associated with rare disease* | | | | | |
| HFE | C/G | Haemochromatosis | Previously described, disease-associated | Damaging | Recessive, incomplete penetrance |
| BTD[20] | C/G | Biotinidase deficiency | Previously described, intermediate phenotype | Damaging | Recessive |
| SLC26A2[21] | C/T | Diastrophic dysplasia | Disease-associated | Damaging | Recessive |
| LAMB3[22] | A/G | Epidermolysis bullosa, junctional | Disease-associated, most common mutation | Truncated protein | Recessive |
| SLC3A1[23] | C/T | Cystinuria | Disease-associated, most common mutation | Damaging | Recessive |
| *Previously described variants of unknown importance in disease-associated genes* | | | | | |
| TMEM43[24] | A/G | ARVD/C | Reported in one of 150 prebands with ARVD/C | Benign | Dominant, incomplete penetrance |
| MYBPC3[25] | C/T | Familial hypertrophic cardiomyopathy | Variant of unknown importance | Intermediate | Dominant, incomplete penetrance |
| *Novel variants potentially associated with rare disease* | | | | | |
| DSP[11] | A/G | ARVD/C | Not found | Damaging | Dominant, incomplete penetrance |
| CDC73[26] | C/T | Hyperparathyroidism, jaw tumour | Not found | Truncated protein | Dominant, loss of heterozygosity |
| CFTR[27] | A/G | Cystic fibrosis | Not found | Damaging | Recessive |
| HFE2 | C/T | Haemochromatosis, juvenile | Not found | Damaging | Recessive |

SNP = single nucleotide polymorphism.
ARVD/C = Arrhythmogenic right-ventricular dysplasia or cardiomyopathy.
*Reference allele in the human genome reference sequence, build 36.7
† Disease associated with inherited mutations in the gene assessed.
‡Mutation databases were assessed for presence of the variant, including UniProt protein variant database, 12 Human Genome Mutation Database, 9 locus-specific mutation databases (curated by the Human Genome Variation Society), Online Mendelian Inheritance in Man, and clinical testing laboratory databases together with associated links.
§Prediction of functional effect of mutation, derived from the substitution effect prediction algorithms, Polymorphism Phenotyping10 and Sorting Intolerant from Tolerant; 8 in-vitro experimental evidence; and assessment of typical mutational mechanisms in other disease gene-associated mutations.
¶Also reported as I1891M; every copy of C allele increases lipoprotein(a) concentration 1-8 SD and risk of coronary artery disease two-to-three fold.
\|\|Inconclusive association in meta-analysis of osteoarthritis-related SNPs, but moderate association with severe hip osteoarthritis.

Analysis of the patient's genome revealed three novel and potentially damaging variants in two related genes that were previously associated with development of hemochromatosis. Subsequent to these findings, detailed review of personal and family history did not identify a history of hemochromatosis in the patient or family members. Echocardiogram results and liver function tests did not show evidence of the disease. Justification for continued surveillance and testing with serum iron studies was explored with the patient.

TABLE 3

Pharmacogenomic variants with summary of effects and level of evidence

| Gene name | | SNP location | Patient genotype | Drug(s) affected | Summary of effects | Level of evidence |
|---|---|---|---|---|---|---|
| SLCO1B1 | Solute carrier organic anion transporter family, member 1B1 | rs4149056 | T/T | HMG-CoA reductase inhibitors (statins) | No increased risk of myopathy | High[32-34] |
| CYP2C19 | Cytochrome P450, family 2, subfamily C, polypeptide 19 | rs4244285 | A/G | Clopidogrel and CYP2C19 substrates | CYP2C19 poor metaboliser, many drugs might need adjustment | High[35] |
| VKORC1 | Vitamin K epoxide reductase complex, subunit 1 | rs9923231 | C/T | Warfarin | Reduced dose needed | High[36] |
| CYP4F2 | Cytochrome P450, family 4, subfamily F, polypeptide 2 | rs2108622 | C/C | Warfarin | Reduced dose needed | High[37] |
| ADRB1 | β1 adrenergic receptor | rs1801252 | A/A | Atenolol, metoprolol | Might be preferable to calcium-channel blockers | High[38,39] |
| SLCO1B1 | Solute carrier organic anion transporter family, member 1B1 | rs11045819 | A/C | Fluvastatin | Good response | Medium[40] |
| HMGCR | HMG-CoA reductase | rs17238540 | T/T | Pravastatin | Patient might have good response | Medium |
| HMGCR | HMG-CoA reductase | rs17244841 | A/A | Pravastatin, simvastatin | No reduced efficacy | Medium |
| ADRB2 | β2 adrenergic receptor, surface | rs1042713 | A/G | β blockers | Other treatment options might be preferable | Medium[41] |
| ADRB2 | β2 adrenergic receptor, surface | rs1042714 | C/C | β blockers | Other treatment options might be preferable | Medium[41,42] |
| CYP2D6 | Cytochrome P450, family 2, subfamily D, polypeptide 6 | rs3892097 rs1800716 | C/C | Metoprolol and other CYP2D6 substrates | Normal CYP2D6 metaboliser | Medium[43] |
| CDKN2A/B | Cyclin-dependent kinase inhibitor 2A/2B | rs10811661 | T/T | Metformin | Reduced likelihood of response | Medium[44] |
| CDKN2A/B | Cyclin-dependent kinase inhibitor 2A/2B | rs10811661 | T/T | Troglitazone | Reduced likelihood of response | Medium[44] |

SNP = single nucleotide polymorphism.
HMG-CoA = 3-hydroxy-3-methylglutaryl-coenzyme A.

TABLE 4

Pharmacogenomic rare and novel non-synonymous damaging variants*

| Gene name | | SNP location | Patient genotype | Drug(s) affected | Effect type | Coding change |
|---|---|---|---|---|---|---|
| NOD2 | Nucleotide-binding oligomerisation domain containing 2 | 16:49303700 | A/G | Infliximab | Pharmacodynamic | V793M |
| NOD2 | Nucleotide-binding oligomerisation domain containing 2 | 16:49302615 | C/T | Infliximab | Pharmacodynamic | S431L |
| SLC15A1 | Solute carrier family 15 (oligopeptide transporter), member 1 | 13:98176691 | C/T | Atorvastatin, fluvastatin, HMG-CoA reductase inhibitors, lovastatin, pravastatin, rosuvastatin, simvastatin | Pharmacokinetic | Y21C |
| HLA-DRB5 | MHC class II, DR beta 5 | 6:32593811 | T/T | Clozapine | Pharmacodynamic | T262K |
| MICA | MHC class I polypeptide-related sequence A | 6:31484467 | C/C | Mercaptopurine, methotrexate | Pharmacodynamic | I14T |
| SLC22A8 | Solute carrier family 22 (organic anion transporter), member 8 | 11:62517376 | C/T | Cimetidine, estrone, anti-inflammatory and antirheumatic products, non-steroids, ibuprofen, indometacin, ketoprofen, methotrexate, phenylbutazone, piroxicam, probenecid, atorvastatin, fluvastatin, HMG-CoA reductase inhibitors, lovastatin, pravastatin, rosuvastatin, simvastatin, adefovir dipivoxil, tenofovir, antineoplastic agents, cyanocobalamin, folic acid, folinic acid, pyridoxine | Pharmacokinetic | R534Q |

SNP = single nucleotide polymorphism.
HMG-CoA = 3-hydroxy-3-methylglutaryl-coenzyme A.
*Predicted to be damaging by PhD-SNP algorithm.[45]

Additionally, the patient had a novel stop mutation in a gene implicated in hyperparathyroidism and parathyroid tumors. This variant might increase probability of future development of hyperparathyroidism or parathyroid tumors through a loss-of-heterozygosity mechanism. Consistent with a variant in a gene previously associated with osteoarthritis, there was a family history of osteoarthritis and the patient reported chronic knee pain without a formal diagnosis.

We noted 63 clinically relevant previously described pharmacogenomic variants and six novel, non-conservative, amino acid changing single nucleotide polymorphisms in genes that are important for drug response. There was a heterozygous null mutation in CYP2C19, the gene product of which is important for metabolism of many drugs, including proton-pump inhibitors, antiepileptic drugs, and the antiplatelet agent clopidogrel. Notably, the rate of cardiovascular events is raised in patients with CYP2C19 loss-of-function mutations who take clopidogrel. Additionally, the patient had two types of distinct genetic variations related to decreased maintenance dosing of warfarin. The patient had the single most important variant in VKORC1 associated with a low maintenance dose, and was homozygous for a CYP4F2 single nucleotide polymorphism that is associated with reduced dosing. Thus, if prescription of warfarin became necessary, loading could be individually tailored for this patient, with lowered expected doses. The patient had several variants that are associated with good response to statins (including reduced risk of myopathy) and one variant suggesting that he might need a raised dose to achieve a good response. Finally, the patient was wild type (with no copy number variations) for genes for important drug-metabolizing enzymes (CYP2D6, CYP2C9, and CYP3A4) affecting hundreds of drug responses.

Figure 3:
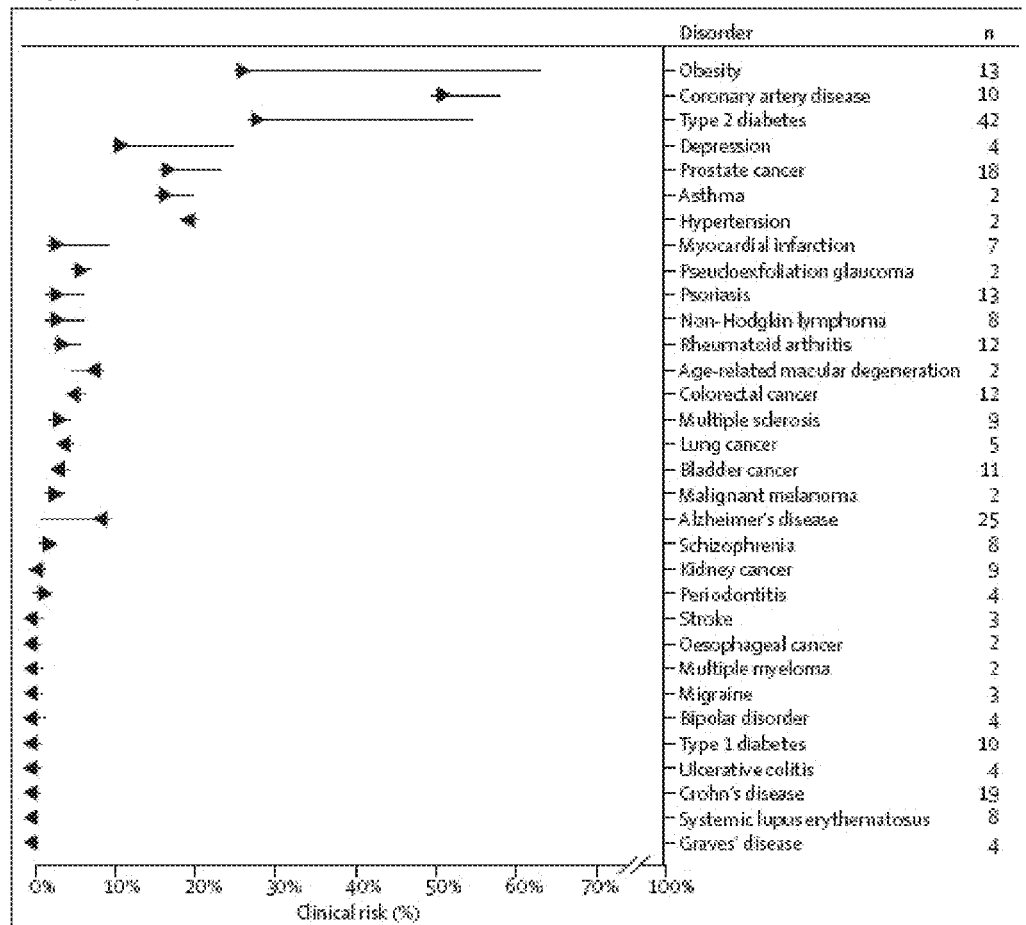
FIG. 3: Clinical risk incorporating genetic-risk estimates for major diseases. We calculated post-test probabilities by multiplying reported pre-test probabilities or disease prevalence (in white men in the patient's age range; web appendix p 16) with a series of independent likelihood ratios for every patient allele. Only 32 diseases with available pre-test probabilities, more than one associated single nucleotide polymorphism, and with reported genotype frequencies are shown. Disorders such as abdominal aortic aneurysm and progressive supranuclear palsy are not listed, because they have only one available single nucleotide polymorphism. Backs of the arrowheads show pre-test probabilities and arrows point in the direction of change in probability. Blue lines show lowered post-test probabilities, and red increased post-test probabilities. n=number of independent single nucleotide polymorphisms used in calculation of post-test probability for that disorder.
Figure 4A:
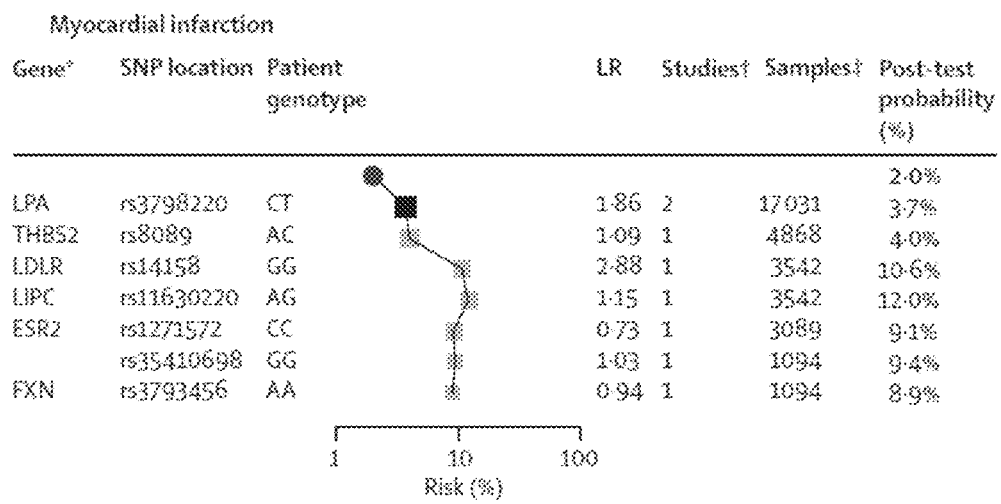
FIG. 4: Contribution of individual alleles to overall risk of myocardial infarction (A), type 2 diabetes (B), prostate cancer (C), and Alzheimer's disease (D) We ordered single nucleotide polymorphisms (SNPs) with associations established from genome-wide association studies in decreasing order of sample size and number of studies showing association. Darkest colors show polymorphisms with the most studies reporting association with disease, and size of boxes scales with the logarithm of the number of samples used to calculate the likelihood ratio (LR). SNPs at the top of every graph are reported in the most and largest studies, and we have the most confidence in their association with disease. We calculated test probabilities using the pre-test estimate as a starting point, and serially stepping down the list of SNPs and calculating an updated post-test probability including the contribution of that genotype. *Gene related to the SNP, if known. †Number of studies reporting an association. ‡Number of samples used to calculate the LR.
Figure 4B:
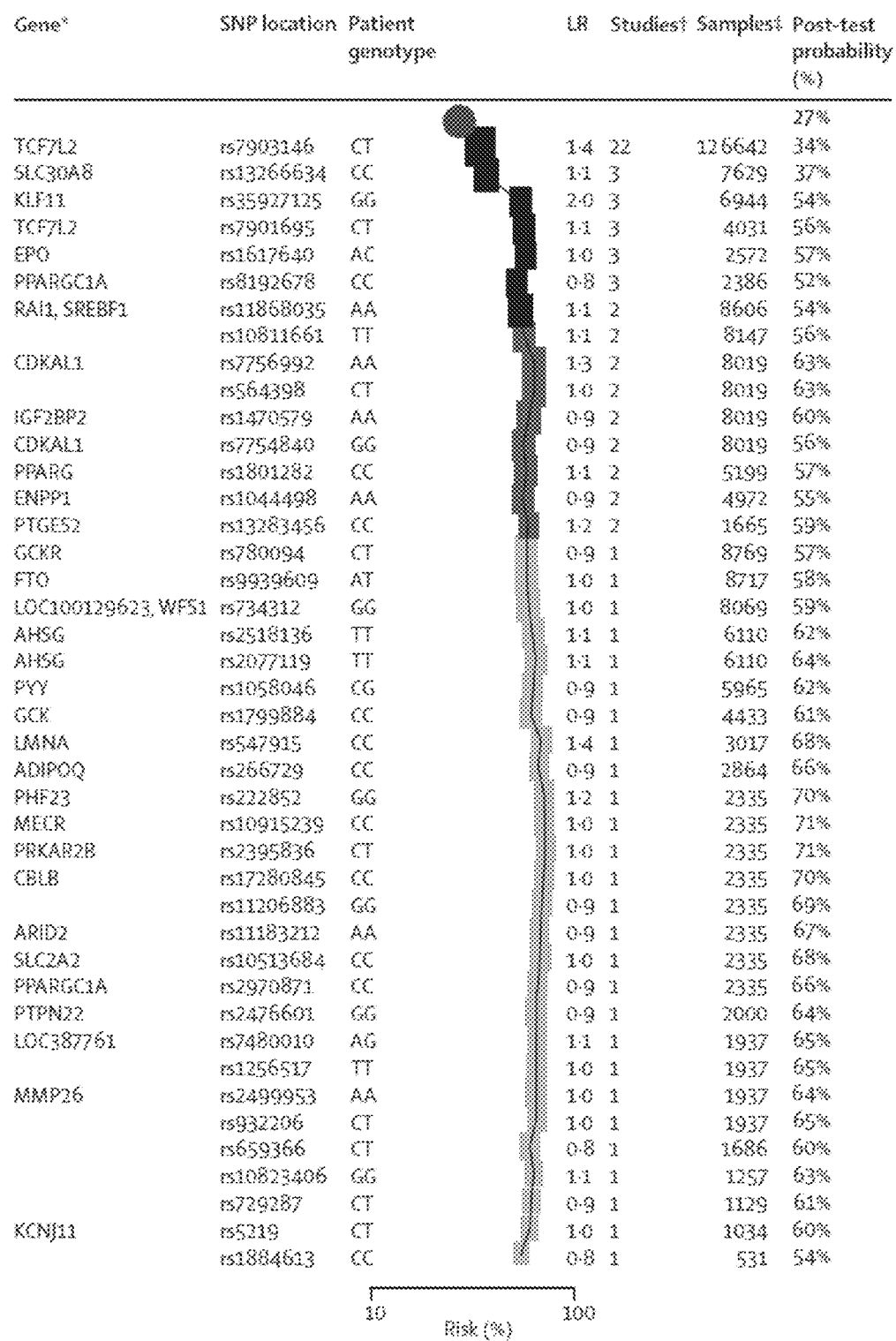
Figure 4C:
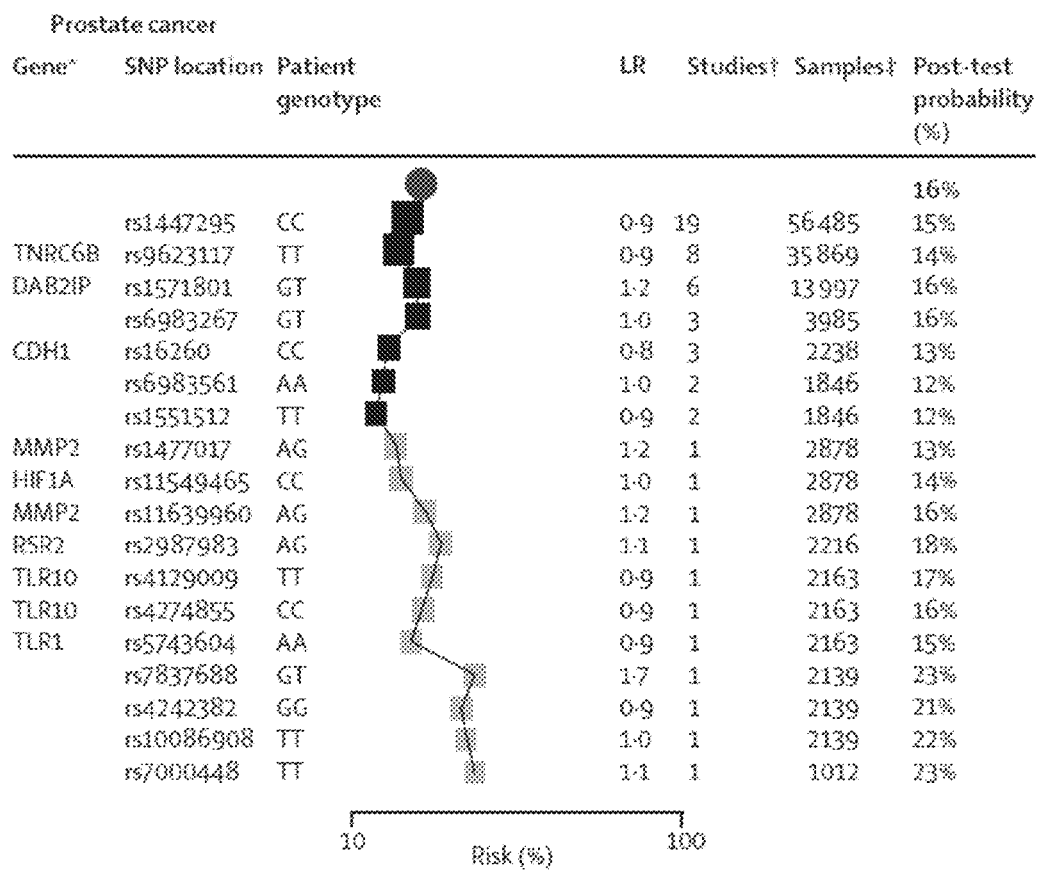
Figure 4D:
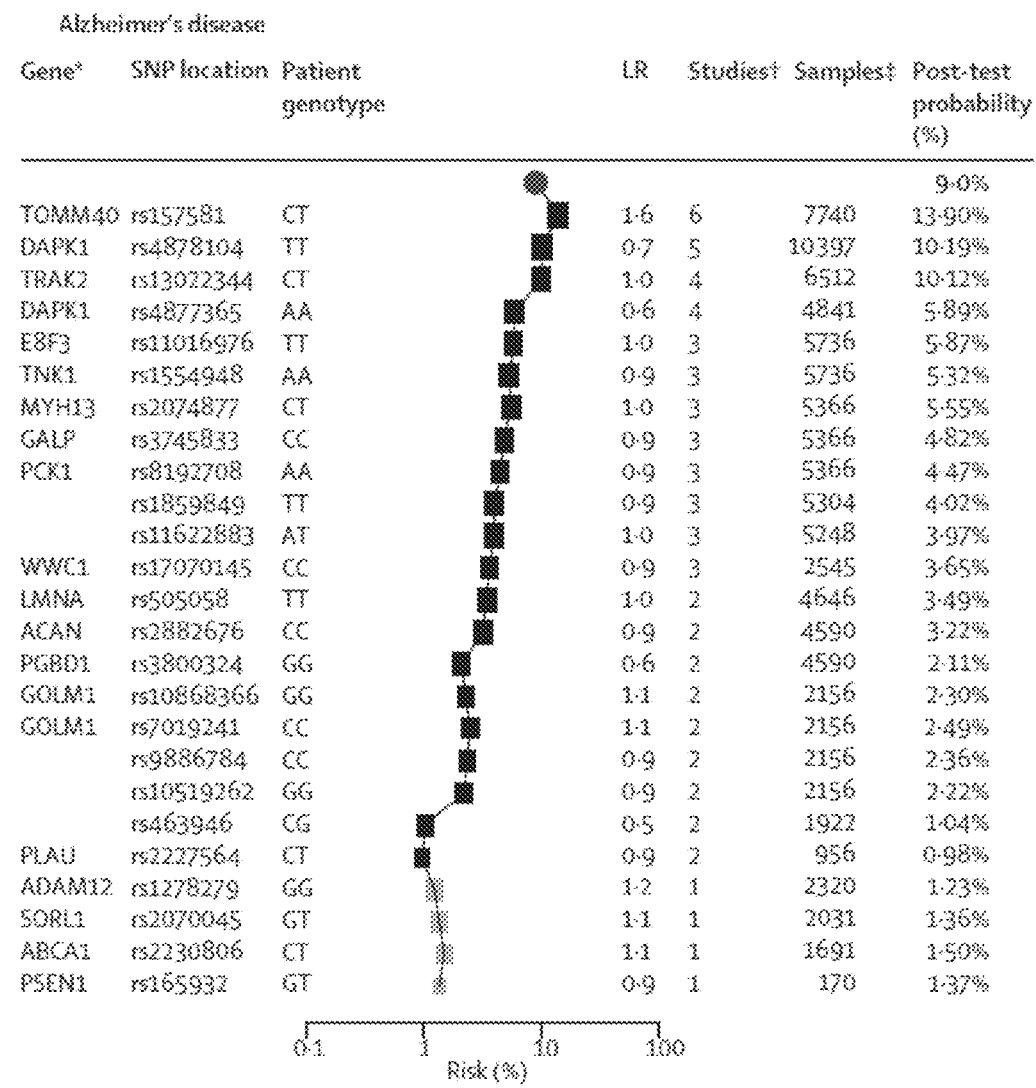

Although genome-wide association studies have provided strong association of many common variants with disease, integration of these small odds ratios in the context of the individual patient remains challenging. In particular, additive or multiplicative models of even strongly associated single nucleotide polymorphisms can add little to the classified status of the patient. Furthermore, these approaches take no account of previous probability of disease. To counter some of these concerns, we adopted established methods from within evidence-based medicine that have rarely been applied to clinical genetics. We estimated pre-test probabilities from referenced sources for 121 diseases. Of the 55 diseases for which we could estimate a post-test probability, genetic risk was consistently increased (LR>2) for eight diseases and decreased (<0-5) for seven diseases (FIG. 3). The advantage of plotting pre-test and post-test probabilities is shown by several examples—e.g., although the patient has increased genetic risk for Graves' disease, because the pretest probability of this disease is very low, post-test probability also remains low. Conversely, although the patient has a low genetic contribution to his risk for prostate cancer, his estimated pre-test probability is high, resulting in a high overall post-test probability.

Raised genetic risk did not always translate into high post-test probability. Post-test probabilities that were an order of magnitude higher or lower than pre-test probabilities were rare. Any decision towards acting on these predictions will necessarily be a function of the post-test probability threshold for action (e.g., the post-test probability of type 2 diabetes), the consequences of action (e.g., regular testing for fasting blood sugar), and the usefulness and effectiveness of action.

Increased genetic risk for myocardial infarction took the form of five single nucleotide polymorphisms associated with susceptibility to myocardial infarction and two protective polymorphisms (FIG. 4). The patient also had risk markers at the locus (9p21) that is most replicated in genome-wide association studies (an example is rs1333049, which is associated with an odds ratio of 1-5 for early onset myocardial infarction—this marker is part of a commercial genetic risk test for myocardial infarction). Furthermore, the patient had one copy of the previously studied variant of LPA encoding the apolipoprotein A precursor. Notably, the patient had a very high lipoprotein(a) concentration (285 nmol/L, reference value <75 nmol/L; table 1), which is associated with increased risk of cardiovascular events. This variant is associated with a five-fold increased median plasma lipoprotein (a) concentration, a 1.7 to two-fold increased risk of coronary artery disease, and a three-fold adjusted odds ratio versus non-carriers for severe coronary artery disease. This polymorphism has been associated with a low number of kringle IV-2 (KIV-2) domain repeats in LPA, high lipoprotein(a) concentrations, and adverse cardio vascular events. Because of the technical limitations of short-read sequencing, a precise estimate of the number of KIV-2 domains in the patient's genome sequence was not established.

Figure 5:
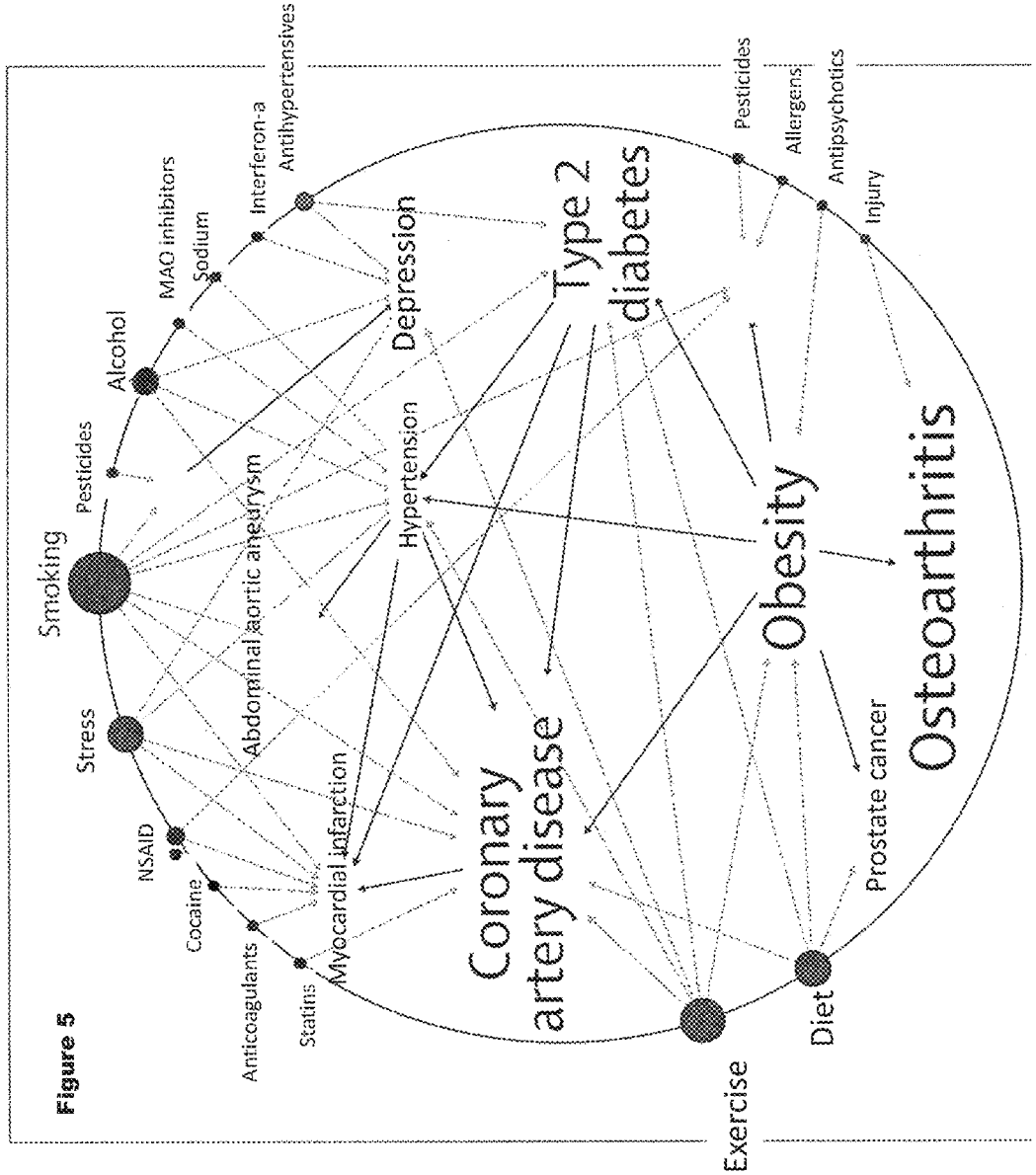
FIG. 5: Gene-environment interaction. A conditional dependency diagram for diseases represented in the patient's genetic-risk profile. Only diseases for which calculable post-test risk probabilities were greater than 10% are shown. For every disease, text size is proportional to post-test risk probability. Solid black arrows are shown between disease names if one disease predisposes a patient to the other. Environmental factors that are potentially modifiable are shown around the circumference, and dashed arrows are shown between an environmental factor and a disease if the factor has been frequently reported in association with the cause of the disease. Text and circle sizes for environmental factors are proportional to the number of diseases that each factor is associated with in the circuit. Color intensity of the circle for each environmental factor represents maximum post-test risk probability amongst diseases directly associated with that factor. NSAID=non-steroidal anti-inflammatory drug. MAO=monoamine oxidase.
Figure 6:
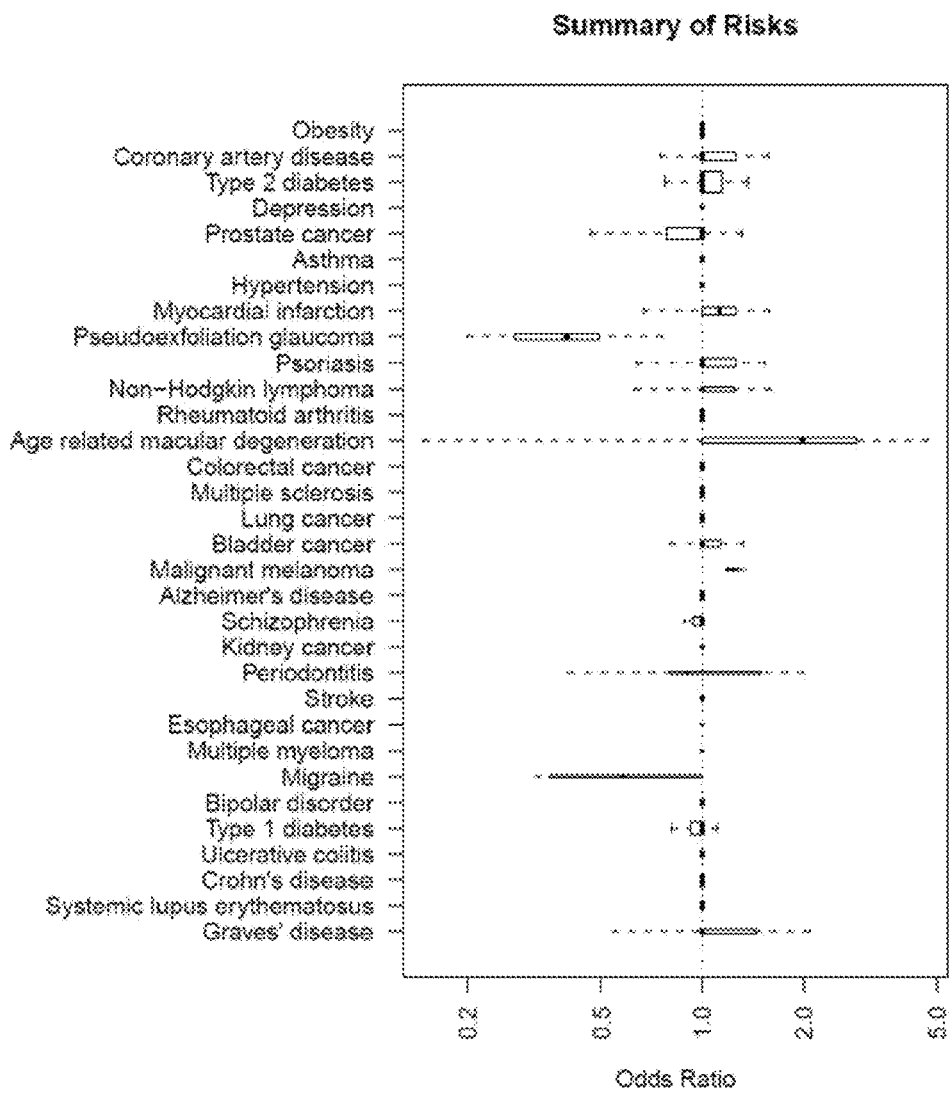
FIG. 6. Box and whiskers plots of odds ratio ranges for each disease featured in FIG. 3A. The thickness of the box scales to the log number of all types of studies.

We placed disease-associated genetic risk into the context of environmental and behavioral modifiers, as well as predisposing disorders (FIG. 5). Diseases that might be independently associated with low genetic risk (e.g., abdominal aortic aneurysm) were assessed in the context of others that could be causally related but for which genetic risk might be higher (e.g., obesity, which predisposes to type 2 diabetes and hypertension). Thus, overall risk could then be assessed with both direct and conditionally dependent information because they were shown together in the circuit. For example, we predicted a reduced risk probability for hypertension of 16.8% (LR 0.81) relative to the general population; however, the patient had a substantially raised genetic risk of obesity (LR 6.28), imparting a high post-test risk of 56.1% for a predisposing risk factor for hypertension. Furthermore, hypertension is associated with several modifiable environmental factors affecting risk either directly (e.g., sodium intake) or conditionally by association with another node in the circuit (e.g., antipsychotic drugs). Although no methods exist for statistical integration of such conditionally dependent risks, interpretation of findings in the context of the causal circuit diagram allows assessment of the combined effect of environmental and genetic risk for every individual.

During genetic counseling, we discussed the possibility that clinical assessment incorporating a personal genome might uncover high risk of a serious disease, including some for which there is no treatment. Additionally, we described the reproductive implications of heterozygous status for autosomal recessive diseases such as cystic fibrosis, which might not be predictable from family history (table 2, FIG. 1). We also warned of increases or decreases in genetic risk for common diseases. We noted that most of the sequence information is difficult to interpret, and discussed error rates and validation processes. Additionally, we discussed that risk alleles might be discovered that have reproductive or familial importance rather than personal importance (such as those for breast or ovarian cancer). We addressed the possibility of discrimination on the basis of genetics. Although a specialized physician can provide information for a patient seeking a genetic test for a specific disease, patients with whole genome sequence data need information about more diseases with a wide clinical range (table 2). For this reason, we offered extended access to clinical geneticists, genetic counselors, and clinical lab directors to interpret the information we presented.

We provide an approach to comprehensive analysis of a human genome in a defined clinical context. We assessed whole-genome genetic risk, focusing on variants in genes that are associated with mendelian disease, novel and rare variants across the genome, and variants of pharmacogenomic importance. Additionally, we developed an approach to the integration of disease risk across several common polymorphisms. The results provide proof that clinically meaningful information can be derived about disease risk and response to drugs in patients with whole genome sequence data.

Prominent aspects of the patient's family history (FIG. 1) were diagnosis of arrythmogenic right ventricular dysplasia or cardiomyopathy in his first cousin (III-3) and the sudden death of his first cousin once removed (IV-1). Our patient shares 12.5% of his genetic information with his first cousin and 6.25% with that relative's son and, although a diagnostic workup would involve targeted sequencing of DNA from these individuals, our analysis uncovered several variants in genes with potential explanatory value. Most were common variants. One gene variant (in MYBPC3) was previously associated with hypertrophic cardiomyopathy, but seems to be a common variant; this exemplifies the limitations of present variant databases. Two rare variants in genes (TMEM43, DSP) previously associated with arrythmogenic right ventricular dysplasia or cardiomyopathy were novel.

Figure 2:
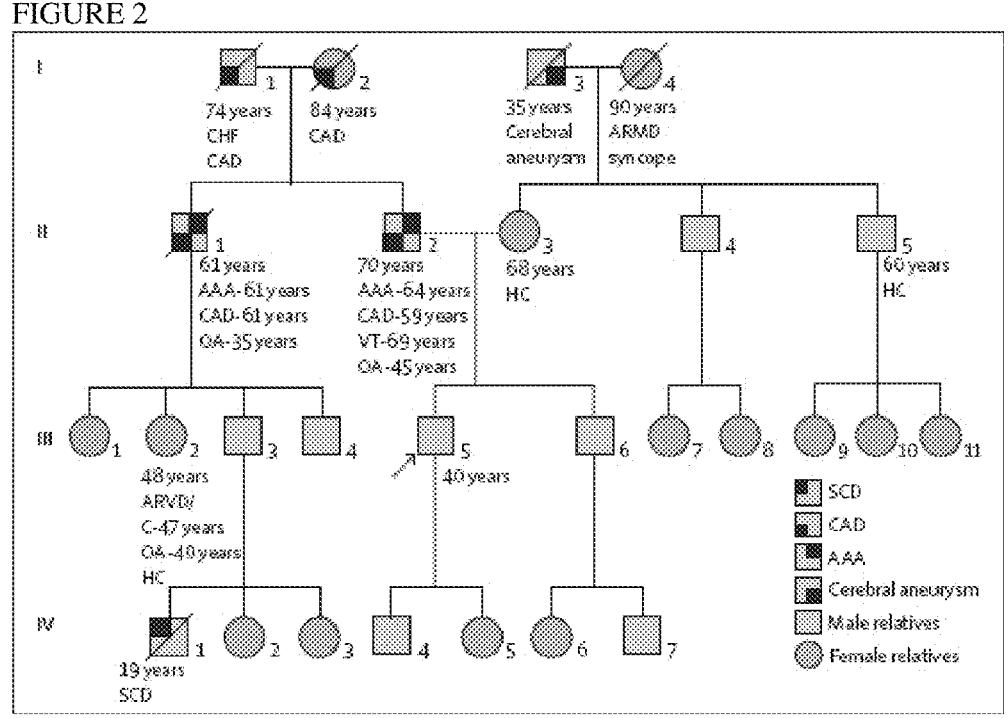
FIG. 2: Patient pedigree. The arrow shows the patient. Diagonal lines show relatives who are deceased. Years are age at death or diagnosis. AAA=abdominal aortic aneurysm. ARMD=age-related macular degeneration. ARVD/C=arrhythmogenic right ventricular dysplasia or cardiomyopathy. CAD=coronary artery disease. CHF=congestive heart failure. HC=hypercholesterolaemia. OA=osteoarthritis. SCD=sudden cardiac death (presumed). VT=paroxysmal ventricular tachycardia.

Our patient reported a prominent family history of vascular disease including aortic aneurysm and coronary artery disease (FIG. 2; individuals II-1, II-2, I-1, I-2). During estimation of the risk of coronary artery disease, we integrated the most replicated risk associations, likelihood ratio projections from published work, and a known variant in LPA that might not have been identified with chip-based genotyping. According to adult treatment panel III guidelines, our patient does not currently have major risk factors for coronary artery disease and would need an LDL concentration higher than 4.9 mmol/L to qualify for lipid-lowering therapy in the USA. However, he is borderline for three major risk factors (one of which is age) and any two of these would lower the threshold for treatment to 4.1 mmol/L (his measured LDL concentration was 4.0 mmol/L). Although no standards yet exist for the incorporation of global genetic risk in cardiovascular risk assessment, physicians are accustomed to incorporating many sources of information in clinical decision making. In this case, the patient's physician considered lifetime genetic risk and likely response to therapy when making the clinical decision to recommend a lipid-lowering drug. The patient's genome includes variants (table 3, table 4) that predict increased likelihood of beneficial effect for statins and reduced risk of the adverse effect of skeletal myopathy. Additionally, attributable risk was substantially reduced in carriers of the LPA risk allele who took aspirin, leading to a discussion between the physician and his patient about the threshold for primary prevention with aspirin therapy.

In view of a predisposition to coronary artery disease and other diseases on which risk is conditionally dependent (FIG. 5), understanding of the patient's potential response to clopidogrel and warfarin might be important for individualization of future medical therapy. The patient is at risk of clopidogrel resistance as a result of his CYP2C19 loss-of-function mutation, and his physician might recommend either an increased dose of clopidogrel in the event of future use, or consideration of new agents with alternative metabolism. By contrast, should the patient develop an indication for warfarin, his genotype at the VKORC1 and CYP4F2 loci suggests that he should take reduced initial doses of warfarin.

By contrast, our patient did not report a family history of hemochromatosis or parathyroid tumors, yet has some genetic risk for these disorders. In consideration of future screening studies, integrated clinical and genetic risks were assessed.

Important limitations remain in our ability to comprehensively integrate genetic information into clinical care. For example, a comprehensive database of rare mutations is needed. Since risk estimates change as studies are completed, a continually updated pipeline is necessary. There are imperfections in all human genomes published to date—false positive and false negative SNP calls, incomplete measurement of structural variation, and little direct haplotype data. Finally, gene-environment interactions are challenging to quantify and have been little studied.

As whole-genome sequencing becomes increasingly widespread, availability of genomic information will no longer be the limiting factor in application of genetics to clinical medicine. Development of methods integrating genetic and clinical data will assist clinical decision making and represent a large step towards individualized medicine. The transition to a new era of genome-informed medical care will need a team approach incorporating medical and genetics professionals, ethicists, and health-care delivery organizations. Further evidence is provided by Dewey et al. (2011) Phased Whole-Genome Genetic Risk in a Family Quartet Using a Major Allele Reference Sequence. PLoS Genet 7(9):e1002280.

Methods

Rare variants. We searched the set of 2.6 million SNPs from the patient for rare variants in coding and important non-coding regions. The heuristic approach to this strategy is presented in FIG. 2. Known rare variants were defined as variants with allele frequency of less than five percent in the Genome Variation Server. Novel variants were defined as variants without validated reference SNP (rs) numbers. We searched for coding variants using four independent analysis tools. Polymorphisms that met these criteria were first annotated using the "Sorting Intolerant from Tolerant" (SIFT) algorithm developed by Henikoff et al, which predicts the effects of non-synonymous polymorphisms on protein function based on homology, conservation, and physical properties of amino acid substitutions. This search yielded 70 predicted damaging mutations of 2795 rare variants found in the patient that had associated SIFT annotations. A similar annotation was performed using the "Polymorphism Phenotyping" (PolyPhen) tool, which predicts the impact of amino acid changes on protein function using an algorithm that incorporates information on site of substitution, i.e., whether an amino acid change occurs in one of several sites of functional importance such as binding sites or trans-membrane regions, sequence alignment, and known protein structural changes. Of 785 rare variants found in patient 0 and described by PolyPhen, 45 were predicted to be possibly damaging. A third query was performed for rare coding variants using the Universal Protein Resource (UniProt) database. This is a manually curated knowledge base consisting of annotated protein sequence variation data with experimentally proven or computer-predicted data to support phenotypic association. Finally, coding region variants that produced premature stop codons or read-throughs in existing stop codons were annotated using the PolyDoms database, which incorporates SNP-phenotype associations from several different sources, including SIFT, PolyPhen, Uniprot, Database of Secondary Structure in Proteins, Protein Databank, and Database of Secondary Structure in Proteins; of 6 rare variants described in this knowledge base, one was associated with a known disease phenotype.

Manual curation was performed for each novel non-synonymous coding variant associated with a known or suspected disease gene, as found in Online Mendelian Inheritance in Man (OMIM). For inherited rare cardiovascular diseases, novel variants in genes currently analyzed by CLIA approved laboratories for clinical genetic testing were evaluated. Manual search of individual international locus specific mutation databases, curated dbSNP and OMIM entries, the public version of the Human Gene Mutation Database, and the published medical literature (PubMed) was performed to determine if prior information was available for putatively novel variants.

SIFT and PolyPhen were used to evaluate the potential effect of novel changes on predicted protein structure and/or the degree of evolutionary conservation of the altered base pair. Putative mRNA splice sites based on consensus coding determination sequences and the sequence of known mature microRNA coding regions were also searched for rare variants by queries matching splice site and miRNA databases to patient variants by chromosome location. This search yielded 394 splice site variants and one rare miRNA variant, which was not found in the putative miRNA seed sequence.

Pharmacogenomics. The compilation of drug-related genotype-phenotype associations was drawn from the Pharmacogenomics Knowledgebase (PharmGKB.org) whose mission is to collect, encode, and disseminate knowledge about the impact of human genetic variations on drug response. From the larger pool of gene-drug-disease literature annotations in PharmGKB, over 2500 manually curated genotypic associations were reduced to approximately 650 genotypic associations with drugs. The PharmGKB curators reviewed the drug-related variant annotations for their clinical relevance to this patient (e.g., patient's genotype, gender, age, family and medical history). A level of evidence was assigned to each variant annotation based on a clinician's appraisal of the impact of the variant based upon the strength of the results in the literature, the effect size of the phenotype, and the availability of drugs to use as alternative treatment. Results include literature evidence for the likelihood of good drug response, inefficacy, side effects, or dosing recommendations based upon the patient's genotype (Table 3).

Disease risk. Disease-associated SNP database. To analyze the disease risk across the spectrum of human disease, a high-quality disease-associated SNP database was built. Starting with a list of all SNPs in dbSNP that were measured in the HapMap 2 and 3 projects, relevant papers were found by searching for rsIDs from within the abstracts of all papers in MEDLINE, eliminating papers covering non-human genetics. A total of 2,671 papers were manually curated and a database generated, including from each full-text paper the disease name (e.g. coronary artery disease), specific phenotype (e.g. acute coronary syndrome in coronary artery disease), study population (e.g. Finnish), case and control population (e.g. 2508 patients with angiographically proven coronary artery disease), genotyping technology, major/minor/risk alleles, odds ratio, 95% confidence interval of the odds ratio, published p-value, and genetic model for each included, statistically significant genotype comparison, including those involving any non-HapMap SNPs within these papers. If not present from the search-based sample, disease associations were recorded from the full text of all papers referenced in the professional version of the Human Gene Mutation Database (HGMD) and the NHGRI GWAS catalog that included dbSNP IDs and included in the association database.

Studies were then separated into two categories: case/control studies (e.g. coronary artery disease vs. control) and cohort studies (e.g. Increase in P-selectin glycoprotein ligand (SELPLG) levels in coronary artery disease vs. control). For each study, the frequency of each genotype and allele in the case and control populations was recorded. As of this writing, 55,258 associations, including 37,409 genotype comparisons, 15,333 case/control genotype frequencies and 7,648 cohort genotype frequencies have been recorded. In the genotype comparison data, 15,333 out of 37,409 total comparisons (40.99%) contained the odds ratio for a specific genotype comparison.

TABLE 5

Sources of SNPs used in calculating disease risk across the disease risk spectrum for the patient's genome sequence.

| Stage | SNPs | Diseases | Publications | Records |
|---|---|---|---|---|
| Disease-associated SNP Database | 9,649 | 813 | 2,671 | 55,258 |
| Data to calculate disease risk based on odds ratio | | | | |
| Limited to SNPs with odds ratio | 4,354 | 456 | 1,590 | 15,333 |
| Limited to disease studies on Caucasian male | 2,325 | 235 | 900 | 6,958 |
| Matched with p0 | 2,067 | 229 | 881 | 5,321 |
| SNPs indicating susceptibility | 403 | 103 | 309 | 1,006 |
| SNPs indicating protection | 344 | 90 | 219 | 803 |
| SNPs identical to reference sequence | 1,350 | 184 | 613 | 3,512 |
| Data to calculate disease risk based on likelihood ratio | | | | |
| Case/control studies | 3,479 | 437 | 1,400 | 10,201 |
| Limited to studies with genotype frequency | 1,657 | 299 | 1,016 | 9,253 |
| Limited to disease studies on Caucasian male | 735 | 141 | 480 | 4,137 |
| Matched with p0 | 524 | 121 | 410 | 1,141 |
| SNPs indicating susceptibility | 584 | 93 | 256 | 584 |
| SNPs indicating protection | 283 | 96 | 243 | 557 |

Categorizing studies on similar diseases and phenotypes. To enable the integration of multiple studies on similar diseases and phenotypes, the disease/phenotype names in our association database were mapped to the Unified Medical Language System (UMLS) Concept Unique Identifiers (CUIs). To improve the quality of matching disease names to UMLS CUI, the best descriptive disease names from the Medical Subject Heading (MeSH) terms were manually selected and associated with each paper during curation, and the matching. UMLS CUIs were then manually examined.

The 55,258 identified associations were categorized into 813 different diseases and phenotypes for 9,649 specific dbSNP IDs. As a comparison, the professional version of HGMD contains 3,725 disease-associated dbSNP IDs, and does not include any genotype comparison information, such as the odds ratio. The NHGRI GWAS catalog includes 2062 records from 379 papers, relating 1683 dbSNP IDs to 251 diseases and phenotypes, including the odds ratio, but does not include corresponding genotype comparisons.

Identifying strand direction in association studies. It was noted that genotypes at the same SNP were reported in both the positive and negative strand in different studies, especially for genes transcribed in the negative strand. For example, the alleles for rs1004819 in IL23R was reported as UT for Crohn's disease and G/A for Ankylosing spondylitis. Strand information was rarely found to be reported in publications, so an algorithm to correctly identify the strand direction automatically was developed to compare study reported major/minor alleles with the major/minor alleles as found in the most similar population to the patient available in HapMap data. A total of 6,196 records were identified that reported genotypes in the negative strand.

Calculating likelihood ratio (LR) of disease risk for SNP genotypes. To calculate the likelihood ratio (LR), the genetic association database was limited to the set of case/control studies reporting associations with diseases in populations that included Caucasian males. We retrieved 4,137 LR for 735 SNPs on 141 diseases, curated from a total of 480 publications. For every disease SNP, we calculated the LR for each genotype using the following equation.

$$LR = \frac{\text{probability of the genotype in the case population}}{\text{probability of the genotype in the control population}}$$

Most publications and related, publicly available datasets report the odds ratios for allele comparisons without exact genotype frequency data, and thus preclude calculation of a likelihood ratio from available data. As a result, many potentially relevant publications were excluded from the provided LR estimates. For this work, likelihood ratios were calculated using only the genotype frequencies reported in the literature.

Pre-test probability for diseases. Pre-test probabilities of lifetime risk of disease were calculated for a wide range of conditions for a person matching the patient's characteristics (age, sex, and ethnicity) using a combination of sources

| Condition | Pretest Probability | Population | Reference |
|---|---|---|---|
| Age related macular degeneration | 8.00% | Caucasians | 33 |
| Alzheimer's disease | 9.00% | Males over 55 | 32 |
| Asthma | 15.50% | White Californian | 37 |
| Bipolar disorder | 1.00% | | 48 |
| Bladder cancer | 3.80% | US white men | 34 |
| Colorectal cancer | 5.88% | Australian men | 21 |
| Coronary artery disease | 50.00% | US men, 40-70 yo | 42 |
| Crohn's disease | 0.20% | Caucasians | 31 |
| Depression | 10.00% | Caucasians | 22 |
| Esophageal cancer | 0.51% | General populace | 29 |
| Graves' disease | 0.14% | Caucasians | 25, 30 |
| Hypertension | 20.00% | | 47 |
| Lung cancer | 4.55% | Australian men | 21 |
| Malignant melanoma | 1.88% | General populace | 34 |
| Migraine | 0.62% | US men | 45 |
| Myocardial infarction | 2.00% | UK Men, 40 yo | 28 |
| Non-Hodgkin lymphoma | 2.09% | Australian men | 21 |
| Obesity | 25.20% | US men, 35-44 yo | 40 |
| Periodontitis | 0.40% | | 23 |
| Prostate cancer | 16.00% | US Caucasians | 34 |
| Pseudoexfoliation glaucoma | 5.00% | | 41 |
| Psoriasis | 2.02% | | 46 |
| Kidney cancer | 1.32% | 40 yo men | 38 |
| Rheumatoid arthritis | 2.80% | US men | 26 |
| Schizophrenia | 1.00% | | 24 |
| Stroke | 0.63% | 45 yo white men, same BP | 43 |
| Systemic lupus erythematosus | 0.10% | Caucasians | 27 |
| Type 1 diabetes | 0.40% | | 44 |
| Type 2 diabetes | 27.00% | | 39 |
| Ulcerative colitis | 0.50% | Caucasians | 36 |

For some conditions, it was possible to match the attributes of the patient very closely, while for many conditions, prevalence and lifetime risk in the general population or in a non-identical (but similar) age or demographic group were used to infer a pre-test probability. The majority of genetic association studies from which LR were derived were case-control, rather than cohort studies which might allow better risk estimates of future disease. Pre and posttest probabilities were used, with recognition of the limitations of this methodology, to provide a more useful construct to display and determine future risk than a simple display of odds ratios alone.

Calculating post-test probability of disease risk for the patient. The patient's full genome sequence was mapped to dbSNP build 129 from the UCSC genome browser to identify dbSNP IDs. Unmapped positions were mapped to dbSNP build 130 to identify additional dbSNP IDs. The LR for the patient's genotype was then determined at each SNP for each disease. For the LR reported in the negative strands, the genotypes were converted into positive strand genotypes before retrieval. We retrieved 1,141 LR on 121 diseases for 524 SNPs.

For each of 121 diseases, the post-test probability of developing disease for the patient was calculated as follows. First, for SNPs with multiple LR from multiple studies, the mean LR was calculated, weighted by the square root of sample sizes. Second, the human genome was partitioned into Haplotype blocks using HapBlock software; for each haplotype block, the highest LR SNP was used. Third, LR from all SNPs were multiplied to report the cumulative LR for the patient. The cumulative LR was calculated for 121 diseases. Finally, the pre-test probability was translated into pre-test odds, multiplied by the cumulative LR to get post-test odds, and then converted to the post-test probability using the following equation. Post-test probabilities were calculable for 55 diseases, while post-test probabilities were calculated using more than one SNP for 32 diseases (FIG. 3A).

Calculating the odds ratios of disease risk. Calculation of the LR of disease risk requires the frequency of three genotypes in the case and control populations. This was available for 1016 out of 2671 papers. In order to include most published genetic associations, the disease risks of the patient were calculated using the odds ratio as extracted from the literature. The allele and genotype frequencies in the case and control population were manually checked to identify the actual comparisons. Study authors were contacted when reported associations and genotype frequencies were discordant from population frequencies. Genetic associations were then retrieved from the disease-associated SNP database for each SNP. Studies reporting associations with diseases (as opposed to other human traits and drug effects) in Caucasian male population, and to those where odds ratios for single SNPs were used for further analysis. A total of 6,958 genetic associations for 2,325 dbSNPs on 235 diseases, curated from 900 publications were used. For each disease/SNP/study combination, the best matching record yielding the highest odds ratio for the patient as compared to the reference sequence was used. In many disease-associated SNPs, the patient has the same genotype as the reference sequence, giving an odds ratio of 1 for the patient versus the reference.

Gene-environment interaction and conditionally dependent risk. A database of established links between diseases and known aetiological factors was obtained as previously described. In brief, Medical Subject Heading (MeSH) annotations in the MEDLINE database were mapped to the Unified Medical Language System (UMLS) semantic network, keeping only those publications with annotations representing diseases and environmental factors.[18] Publications that contained a major MeSH term and sub-heading (indicating a primary focus of the paper) on the "etiology" or "chemical induction" of a disease were selected. These publications also had to contain a major MeSH term and sub-heading on the "adverse effect" or "complication" or "toxicity" or "poisoning" related to an environmental factor. The frequency of finding each disease-factor association across the entire MEDLINE corpus was noted. For the purpose of constructing the aetiological "circuit diagram", this database was filtered to aetiological links that were curated from 10 or more independent publications. For example, if 27 publications in MEDLINE contained the MeSH annotations "Renal Dialysis/adverse effects" and "Atherosclerosis/etiology", and if only 25 publications with "Dietary Fats/adverse effects" and "Atherosclerosis/etiology", then dialysis was considered as an environmental factor slightly more strongly associated with atherosclerosis than dietary fats.

| Chr: Position | Ref Call | Allele Calls | Curated Comments | Gene Symbol | Substitution | MIM Morbid Status | Curated PMID | SIFT Prediction | PolyPhen prediction | rsID |
|---|---|---|---|---|---|---|---|---|---|---|
| Rare nsSNPs with rsIDs, likely disease associated | | | | | | | | | | |
| 3:185553282 | C | CG | disease associated | CLCN2 | E718D | EPILEPSY, CHILDHOOD ABSENCE, 3 | 17580110 | TOLERATED | benign | rs2228292 |
| 1:115037580 | G | AG | disease associated | AMPD1 | Q12* | ADENOSINE MONO-PHOSPHATE DEAMINASE 1 | 1631143 | N/A | premature stop | rs17602729 |
| 17:71338086 | G | AG | disease associated | UNC13D | R928C | HEMOPHAGOCYTIC LYMPHOHISTIOCYTOSIS, FAMILIAL, 3 | 16825436 | DAMAGING | — | rs35037984 |
| 10:54201248 | G | AG | disease associated | MBL2 | R52C | LECTIN, MANNOSE-BINDING, SOLUBLE, 2 | 8206524 | DAMAGING | probably damaging | rs5030737 |
| 11:68318904 | C | CT | disease associated | CPT1A | A275T | CARNITINE PALMITOYL-TRANSFERASE I DEFICIENCY | 14517221 | TOLERATED | — | rs2229738 |
| 5:131699533 | G | GT | disease associated | SLC22A4 | G462V | INFLAMMATORY BOWEL DISEASE 1 | 15459889 | DAMAGING | — | rs4646201 |
| 1:94249055 | T | AT | VUS | ABCA4 | N1868I | MACULAR DEGENERATION, AGE-RELATED, 2 | | DAMAGING | probably damaging | rs1801466 |
| 6:15631427 | G | AG | disease associated | DTNBP1 | P272S | INCREASED RISK OF COLORECTAL CANCER | 17000706 | Damaging LC | probably damaging | rs17470454 |
| 15:74365817 | G | AG | modifier damaging | ETFA | T171I | MULTIPLE ACYL-CoA DEHYDROGENASE DEFICIENCY | 10356313 | DAMAGING | probably damaging | rs1801591 |
| Rare nsSNPs not in dbSNP in genes associated with disease | | | | | | | | | | |
| 10:13380242 | G | AG | disease associated | PHYH | P29S | REFSUM DISEASE | 10767344 | TOLERATED | — | no rs |
| 3:185553595 | C | CT | disease associated | CLCN2 | R688Q | EPILEPSY, CHILDHOOD ABSENCE, 3 | 15505175 | TOLERATED | — | no rs |
| 17:7925204 | G | AG | disease associated | ALOX12B | P127S | ICHTHYOSIFORM ERYTHRODERMA, CONGENITAL, NONBULLOUS, 1 | 16116617 | TOLERATED | — | no rs |
| 16:1353032 | C | CT | disease associated | GNPTG | T286M | MUCOLIPIDOSIS III GAMMA | 19370764 | TOLERATED | — | no rs |
| 1:115032777 | G | AG | disease associated | AMPD1 | P48L | ADENOSINE MONO-PHOSPHATE DEAMINASE 1 | 1631143 | DAMAGING | — | no rs |
| X:100545469 | G | AG | heterozygote X | GLA | Q119* | FABRY DISEASE | 8875188 | N/A | premature stop | no rs |
| 2:178253812 | C | CT | disease associated | PDE11A | R804H | PIGMENTED NODULAR ADRENOCORTICAL DISEASE, PRIMARY, 2 | 17178847 | DAMAGING | — | no rs |
| 1:94289842 | C | CG | disease associated | ABCA4 | G863A | STARGARDT DISEASE | 9054934 | DAMAGING | — | no rs |
| 1:94301301 | C | CT | disease associated | ABCA4 | R572Q | STARGARDT DISEASE | 9973280 | DAMAGING | — | no rs |

-continued

| Novel nsSNPs predicted damaging in genes associated with disease | | | | | | | | | |
|---|---|---|---|---|---|---|---|---|---|
| 3:130105612 | G | AG | novel & damaging | ACAD9 | A326T | ACYL-CoA DEHY-DROGENASE FAMILY, MEMBER 9, DEFICIENCY OF | DAMAGING | — | no rs |
| 16:49303700 | G | AG | novel & damaging | CARD15 | V793M | SYNOVITIS, GRANULOMATOUS, WITH UVEITIS AND CRANIAL NEUROPATHIES | DAMAGING | — | no rs |
| 16:49302615 | C | CT | novel & damaging | CARD15 | S431L | SYNOVITIS, GRANULOMATOUS, WITH UVEITIS AND CRANIAL NEUROPATHIES | Damaging LC | — | no rs |
| 12:54774480 | C | CT | novel & damaging | ERBB3 | H578Y | LETHAL CONGENITAL CONTRACTURE SYNDROME 2 | DAMAGING | — | no rs |
| 6:142801120 | G | CG | novel & damaging | GPR126 | G1166A | STATURE AS A QUANTITATIVE TRAIT | Damaging LC | — | no rs |
| 17:68708988 | G | AG | novel stop | COG1 | W476* | CONGENITAL DISORDER OF GLYCOSYLATION, TYPE IIg | N/A | — | no rs |
| 7:93888305 | C | CT | novel & damaging | COL1A2 | P782S | EHLERS-DANLOS SYNDROME, TYPE VII | DAMAGING | benign | no rs |
| 19:15151236 | G | GT | novel & damaging | NOTCH3 | H1133Q | CEREBRAL ARTERIOPATHY, AUTOSOMAL DOMINANT, WITH SUBCORTICAL INFARCTS | DAMAGING | — | no rs |
| 10:103817037 | C | CT | novel & damaging | HPS6 | R606C | HERMANSKY-PUDLAK SYNDROME | Damaging LC | — | no rs |
| 9:106527820 | C | CT | novel & damaging | ABCA1 | G836E | TANGIER DISEASE | DAMAGING | — | no rs |
| 9:123102076 | C | CT | novel & damaging | GSN | A39V | AMYLOIDOSIS, FINNISH TYPE | Damaging LC | — | no rs |
| 20:60938927 | G | AG | novel & damaging | COL9A3 | G551R | EPIPHYSEAL DYSPLASIA, MULTIPLE, 3 | DAMAGING | — | no rs |
| 1:207869854 | T | AT | novel & damaging | LAMB3 | D328V | EPIDERMOLYSIS BULLOSA, JUNCTIONAL, NON-HERLITZ TYPE | DAMAGING | — | no rs |
| 1:207869851 | G | GT | novel & damaging | LAMB3 | P329H | EPIDERMOLYSIS BULLOSA, JUNCTIONAL, NON-HERLITZ TYPE | DAMAGING | — | no rs |
| 7:94086166 | T | GT | novel & damaging | SGCE | N168H | MYOCLONIC DYSTONIA | DAMAGING | — | no rs |
| 6:32913392 | G | AG | novel & damaging | TAP2 | P170S | BARE LYMPHOCYTE SYNDROME, TYPE I | DAMAGING | — | no rs |
| 1:221350692 | G | AG | novel & damaging | TLR5 | L769F | AUTOIMMUNE DISEASE | DAMAGING | — | no rs |
| X:37472427 | T | GG | novel & damaging | XK | Y370D | KELL BLOOD GROUP PRECURSOR | DAMAGING | — | no rs |
| 16:46761579 | T | AT | novel & damaging | ABCC11 | N1277Y | EAR WAX, WET/DRY | DAMAGING | — | no rs |
| 3:51998064 | G | AG | novel & damaging | ACY1 | G387E | AMINOACYLASE 1 DEFICIENCY | DAMAGING | — | no rs |
| 20:32342227 | G | AG | novel & damaging | AHCY | P246L | S-ADENOSYLHOMOCYSTEINE HYDROLASE | Damaging LC | — | no rs |
| 1:33251518 | G | CG | novel & damaging | AK2 | H191D | RETICULAR DYSGENESIA | DAMAGING | — | no rs |

-continued

| Chr: Position | Ref Call | Allele Calls | | Gene Symbol | Substitution | Disease | Status | | rsID |
|---|---|---|---|---|---|---|---|---|---|
| 19:47177813 | A | AT | novel & damaging | ATP1A3 | F401L | DYSTONIA 12 | DAMAGING | — | no rs |
| 17:17872345 | C | CT | novel & damaging | ATPAF2 | E84K | ENCEPHALOCARDIOMYOPATHY, MITOCHONDRIAL, NEONATAL, DUE TO ATP SYNTHASE | DAMAGING | — | no rs |
| 5:70344018 | C | CT | novel & damaging | BIRC1 | A161T | SPINAL MUSCULAR ATROPHY, TYPE I | Damaging LC | — | no rs |
| 16:54420192 | G | AG | novel & damaging | CES1 | S83L | CARBOXYLESTERASE 1 | DAMAGING | — | no rs |
| 19:446690390 | G | AG | novel & damaging | DLL3 | R585Q | SPONDYLOCOSTAL DYSOSTOSIS, AUTOSOMAL RECESSIVE 1 | Damaging LC | — | no rs |
| 11:65392614 | G | AG | novel & damaging | EFEMP2 | R264C | CUTIS LAXA, AUTOSOMAL RECESSIVE, TYPE I | DAMAGING | — | no rs |
| 4:5761129 | C | CT | novel & damaging | EVC2 | G5S | WEYERS ACROFACIAL DYSOSTOSIS | Damaging LC | — | no rs |
| 17:1907902 | C | AC | novel & damaging | HIC1 | P409T | MILLER-DIEKER LISSENCEPHALY SYNDROME | Damaging LC | — | no rs |
| 22:48854832 | G | GT | novel & damaging | MLC1 | N218K | MEGALENCEPHALIC LEUKOENCEPHALOPATHY WITH SUBCORTICAL CYSTS | Damaging LC | — | no rs |
| 7:56054917 | G | AG | novel & damaging | PSPH | R49W | PHOSPHOSERINE PHOSPHATASE | DAMAGING | — | no rs |
| 19:3722586 | G | AG | novel & damaging | RAX2 | P52L | MACULAR DEGENERATION, AGE-RELATED, 1 | DAMAGING | — | no rs |
| 11:124245273 | C | CT | novel & damaging | ROBO3 | R257C | GAZE PALSY, FAMILIAL HORIZONTAL, WITH PROGRESSIVE SCOLIOSIS | DAMAGING | — | no rs |
| 6:45404063 | C | CT | novel & damaging | RUNX2 | P9L | CLEIDOCRANIAL DYSPLASIA | Damaging LC | — | no rs |
| 5:289678 | G | AG | novel & damaging | SDHA | A466T | MITOCHONDRIAL COMPLEX II DEFICIENCY | DAMAGING | — | no rs |
| 9:71055808 | C | CT | novel & damaging | TIP2 | S1010F | HYPERCHOLANEMIA, FAMILIAL | Damaging LC | — | no rs |
| 17:38186352 | G | AG | novel & damaging | WNK4 | G37E | PSEUDOHYPOALDOSTERONISM, TYPE II | Damaging LC | — | no rs |

| Rare splice site variants in disease associated genes |||||||
|---|---|---|---|---|---|---|
| Chr: Position | Ref Call | Allele Calls | Splice Site | Gene Symbol | Substitution | MIM Morbid Status | rsID |
| 1:115037580 | G | AG | exon 3'-2 | AMPD1 | Q12* | ADENOSINE MONOPHOSPHATE DEAMINASE 1 | rs17602729 |
| 9:139768563 | C | CT | exon 3'-1 | EHMT1 | L425L | CHROMOSOME 9q34.3 DELETION SYNDROME | no rs |
| 3:48580072 | C | CT | exon 5'-1 | COL7A1 | G2662E | EPIDERMOLYSIS BULLOSA WITH CONGENITAL LOCALIZED ABSENCE OF SKIN | no rs |
| 6:15631427 | G | AG | exon 5'-2 | DTNBP1 | 9272S | HERMANSKY-PUDLAK SYNDROME | rs17470454 |
| 5:142573845 | C | TT | exon 3'-1 | ARHGAP26 | N785N | FUVENILE MYELOMONOCYTIC LEUKEMIA | rs258819 |
| 1:94289842 | C | CG | intron 3' 1 | ABCA4 | G863A | MACULAR DEGENERATION, AGE-RELATED, 2 | no rs |
| 13:30719992 | T | CC | exon 5'-2 | B3GALTL | H116H | PETERS-PLUS SYNDROME | rs4943266 |

| Rare microRNA variant |||||||
|---|---|---|---|---|---|---|
| SNP_loc | Ref Call | Allele calls | pre_miRNA_position | miRNA_acc | miRNA_id | Seed sequence | Distance_from_seed_start |
| 13:24736585 | G | AA | 30 | MI0011282 | hsa-mir-2276 | no | −85 |

SUPPLEMENTAL TABLE 3a

Pharmacogenomic effects that increase likelihood of positive effects, no side effects or predictable dosing.

| Drug Class | Drug | Summary | Level of Evidence | PMID | Gene | Gene Name | rsID | Variant common name | Patient Genotype |
|---|---|---|---|---|---|---|---|---|---|
| lipid-modifying agent | HMG CoA Reductase Inhibitors (statins) | No increased risk of myopathy | High | 12811365; 17177112; 18650507 | SLCO1B1 | solute carrier organic anion transporter family, member 1B1 | rs4149056 | SLCO1B1: 521T>C, SLCO1B1:*5; SLCO1B1:V174A | T/T |
| antidepressant | Desipramine; Fluoxetine | Depression may improve more than average | Medium | 19414708 | BDNF | brain-derived neurotrophic factor | rs61888800 | | G/G |
| lipid-modifying agent | Fluvastatin | Good response | Medium | 18781850 | SLCO1B1 | solute carrier organic anion transporter family, member 1B1 | rs11045819 | SLCO1B1: 463C>A | A/C |
| various | Metoprolol and other CYP2D6 substrates | Normal CYP2D6 metabolizer | Medium | 19037197 | CYP2D6 | cytohrome P450, family 2, subfamily D, polypeptide 6 | rs3892097 rs1800716 | CYP2D6: 1846G>A, part of CYP2D6*4 | C/C |
| lipid-modifying agent | Pravastatin | May have good response | Medium | 15199031 | HMGCR | 3-hydroxy-3-methylglutaryl-Coenzyme A reductase | rs17238540 | SNP 29 | T/T |
| lipid-modifying agent | Pravastatin, Simvastatin | No reduced efficacy | Medium | 15199031 | HMGCR | 3-hydroxy-3-methylglutaryl-Coenzyme A reductase | rs17244841 | SNP 12 | A/A |
| Stimulant | Caffeine | No increased risk of heart problems with caffeine | Low | 16522833 | CYP1A2 | cytochrome P450, family 1, subfamily A, polypeptide 2 | rs762551 | CYP1A2*1F | A/A |
| calcium channel blockers | Calcium channel blockers | No increased risk of Torsades de Pointe | Low | 15522280 | KCNH2 | potassium voltage-gated channel, subfamily H (eag-related), member 2 | rs36210421 | KCNH2: Arg1047Leu | C/C |
| anti-seizure | Carbamazepine | SNP is part of protective haplotype for hyperensitivity to carbamazepine | Low | 16538175 | HSPA1A | heat stock 70 kDa protein 1A | rs1043620 | HSPA1A + 438 C/T | T/T |
| anti-retroviral | Neviraprine | Reduced risk of hepatoxicity | Low | 16912957 | ABCB1 | ATP-binding cassette, sub-family B (MDR/TAP), member 1 | rs1045642 | ABCB1:3435C>T (3853C>T dbSNP 130) | A/G |
| anti-retroviral | Efavirenz; Nevirapine | Reduced risk of hepatoxicity | Low | 16912956 | ABCB1 | ATP-binding cassette, sub-family B (MDR/TAP), member 1 | rs1045642 | ABCB1:3435C>T (3853C>T dbSNP 130) | A/G |
| antianemic | Epoetin Alfa | Lower dose of iron and epo required | Low | 18025780 | HFE | hemochromatosis | rs1799945 | HFE:His63Asp | C/G |
| anti-histamine | Fexofenadine | Average blood levels expected | Low | 11503014 | ABCB1 | ATP-binding cassette, sub-family B (MDR/TAP), member 1 | rs1045642 | ABCB1:3435C>T (3853C>T dbSNP 130) | A/G |
| anti-hypertensive | Irbesartan | Irbesartan may work better than beta-blocker | Low | 15453913 | APOB | apolipoprotein B (including Ag(x) antigen) | rs1367117 | APOB:711C>T | A/G |
| anti-psychotic | Lithium | Increased likelihood of response | Low | 18403563 | CACNG2 | calcium channel, voltage-dependent, gamma submit 2 | rs5750285 | | C/C |
| anti-depressant | Paroxetine | May have improved response | Low | 17913323 | ABCB1 | ATP-binding cassette, sub-family B (MDR/TAP), member 1 | rs2032582 | ABCB1: 2677G>T/A, Ala893Ser/Thr | A/C |

SUPPLEMENTAL TABLE 3a-continued

Pharmacogenomic effects that increase likelihood of positive effects, no side effects or predictable dosing.

| Drug Class | Drug | Summary | Level of Evidence | PMID | Gene | Gene Name | rsID | Variant common name | Patient Genotype |
|---|---|---|---|---|---|---|---|---|---|
| anti-Parkinsonism | Pramipexole | More likely to respond | Low | 19396436 | DRD3 | dopamine receptor D3 | rs6280 | DRD3:Ser9Gly | T/T |
| lipid-modifying agent | Pravastatin | No reduced efficacy | Low | 15226675 | SLCO1B1 | solute carrier organic anion transporter family, member 1B1 | rs4149015 | SLCO1B1: (−11187) G>A | G/G |
| anti-diabetic | Rosiglitazone | May have good response | Low | 18693052 | LPIN1 | lipin 1 | rs10192566 | | C/G |
| muscle relaxant | Succinylcholine | No increased risk of apnea | Low | 1415224 | BCHE | butyryl-cholinesterase | rs28933389 | BCHE:Thr243Met, Fluoride resistant I | G/G |
| muscle relaxant | Succinylcholine | No increased risk of apnea | Low | 1415224 | BCHE | butyryl-cholinesterase | rs28933390 | BCHE:Gly390Val, Fluoride resistant II | C/C |

SUPPLEMENTAL TABLE 3b

Pharmacogenomic effects that increase likelihood of adverse events, lack of efficacy, uncertain dosing.

| Drug Class | Drug | Summary | Level of Evidence | PMID | Gene | Gene Name | rsID | Variant common name | Patient Genotype |
|---|---|---|---|---|---|---|---|---|---|
| antiplatelets | Clopidogrel & CYP2C19 substrates | CYP2C19 poor metabolizer, many drugs may need adjustment. | High | 19106584 | CYP2C19 | cytochrome P450, family 2, subfamily C, polypeptide 19 | rs4244285 | CYP2C19: G681A (*2) | A/G |
| anti-coagulant | Warfarin | Requires lower dose | High | 15888487 | VKORC1 | vitamin K epoxide reductase complex, subunit 1 | rs9923231 | VKORC1: −1639G>A | C/T |
| anti-coagulant | Warfarin | Requires lower dose | High | 19270263 | CYP4F2 | cytochrome 9450, family 4, subfamily F, polypeptide 2 | rs2108622 | CYP4F2: V433M | C/C |
| antidiabetic | Metformin | Less likely to respond | Medium | 18544707 | CDKN2A/B | cyclin-dependent kinase inhibitor 2A/2B | rs10811661 | rs10811661 | T/T |
| antidiabetic | Troglitazone | Less likely to respond | Medium | 18544707 | CDKN2A/B | cyclin-dependent kinase inhibitor | | | T/T |
| anticancer | Cisplatin | Increased risk of nephroroxicity | Low | 19625999 | SLC22A2 | solute carrier family 22 (organic cation transporter), member 2 | rs316019 | SLC22A2: 808G>T | C/C |
| anti-depressant | Citalopram | May increase risk of suicidal ideation during therapy | Low | 17898344 | GRIA3 | glutamate receptor, ionotrophic, AMPA 3 | rs4825476 | | G/G |
| anti-depressant | Escitalopram; Nortriptyline | Depression may not respond as well | Low | 19365399 | NR3C1 | nuclear receptor subfamily 3, group C, member 1 (glucocorticoid receptor) | rs10482633 | | G/T |
| analgesic; opiate | Morphine | May require higher dose for pain relief | Low | 17156920 | COMT | catechol-O-methyltransferase | rs4680 | COMT: 721G>A Val158Met | A/G |
| anticancer | Paclitaxel | Cancer may respond less well | Low | 18836089 | ABCB1 | ATP-binding cassette, sub-family B (MDR/TAP), member 1 | rs1045642 | ABCB1: 3435C>T (3853C>T dbSNP 130) | A/G |
| lipid-modifying agent | Pravastatin | May require higher dose | Low | 15116054 | SLCO1B1 | solute carrier organic anion transporter family, member 1B1 | rs2306283 | SLCO1B1: N130D | A/G |
| anti-arrhythmic, anti-hypertensive | Talinolol | May require higher dose | Low | 18334920 | ABCC2 | ATP-binding cassette, sub-family C (CFTR/MRP), member 2 | rs2273697 | ABCC2: c.1249G>A, ABCB2: V417I | A/G |
| anti-erecrile dysfunction, anti-hypertensive | Sildenafil | May not respond as well | Low | 12576843 | GNB3 | guanine nucleotide binding protein (G protein), beta polypeptide 3 | rs5443 | | C/T |

SUPPLEMENTAL TABLE 3c

Pharmacogenotnic effects that are mixed and hard to integrate.

| Drug Class | Drug | Summary | Level of Evidence | PMID | Gene | Gene Name | rsID | Variant common name | Patient Genotype |
|---|---|---|---|---|---|---|---|---|---|
| anti-arrhythmic, anti-hypertensive | Atenolol | May be better than angiotensin receptor blockers | Low | 15453913 | LDLR | low density lipoprotein receptor | rs688 | LDLR: 16730C>T | C/C |
| anti-arrhythmic, anti-hypertensive | Atenolol; Metoprolol | May be better than calcium-channel blockers | High | 18615004 12844134 16815314 | ADRB1 | adrenergic, beta-1-, receptor | rs1801252 | ADRB1: Ser49Gly | A/A |
| anti-arrhythmic, anti-hypertensive | Beta blockers | Other options may be preferred | Medium | 16189366 | ADRB2 | adrenergic, beta-2-, receptor, surface | rs1042713 | ADRB2: Arg16Gly | A/G |
| anti-arrhythmic, anti-hypertensive | Beta blockers | Other options may be preferred | Medium | 12835612 16189366 | ADRB2 | adrenergic, beta-2-, receptor, surface | rs1042714 | ADRB2: Gln27Glu; 79C>G; Gln27 | C/C |
| antipsychotic | Iloperidone | Likely increased risk for QT prolongation | Low | 18521091 | BRUNOL4 | bruno-like 4, RNA binding protein (*Drosophila*) | rs4799915 | | C/T |
| antipsychotic | Iloperidone | Likely decreased risk for QT prolongation | Low | 18521091 | CERKL | ceramide kinase-like | rs993648 | | C/T |
| antipsychotic | Iloperidone | More likely to respond | Low | 18303965 | CNTF | ciliary neurotrophic factor | rs1800169 | CNTF: FS63TER | G/G |
| antipsychotic | Iloperidone | Likely increased risk for QT prolongation | Low | 18521091 | NRG3 | neurogulin 3 | rs4933824 | | G/G |
| antipsychotic | Iloperidone | Likely increased risk for QT prolongation | Low | 18521091 | NUBPL | nucleotide binding protein-like | rs7142881 | | A/G |
| antipsychotic | Iloperidone | Likely increased risk for QT prolongation | Low | 18521091 | PALLD | palladin, cytoskeletal associated protein | rs17054392 | | T/T |
| antipsychotic | Iloperidone | Likely increased risk for QT prolongation | Low | 18521091 | SLCO3A1 | solute carrier organic anion transporter family, number 3A1 | rs3924426 | | T/T |
| anticancer, anti-inflammatory/autoimmue | Methotrexate | Less likely to respond | Low | 19093297 | ABCB1 | ATP-binding cassette, sub-family B (MDR/TAP), member 1 | rs1045642 | ABCB1: 3435C>T (3853C>T dbSNP 130) | A/G |
| anticancer, anti-inflammatory/autoimmue | Methotrexate | More likely to respond | Low | 18256692 | ABCG2 | ATP-binding cassette, sub-familyG (WHITE), member 2 | rs17731538 | | A/G |
| anticancer, anti-inflammatory/autoimmue | Methotrexate | More likely to respond | Low | 16572443 | MTHFR | 5,10-methylenetetrahydrofolate reductase (NADPH) | rs1801133 | MTHFR: 677C>T | C/C |
| anticancer, anti-inflammatory/autoimmue | Methotrexate | More likely to be toxic and to discontinue | Low | 17410198 | SLC19A1 | solute carrier family 19 (folate transporter), member 1 | rs1051266 | SLC19A1: 80A>G His27Arg | C/T |
| anticancer, anti-inflammatory/autoimmue | Methotrexate | More likely to have adverse events and toxicity | Low | 16572443 | MTHFR | 5,10-methylenetetrahydrofolate reductase (NADPH) | rs1801131 | MTHFR: 1298A>C | G/T |
| antipsychotic | Olanzapine | Less likely to gain weight | Low | 19193342 | ADRB3 | adrenergic, beta-3-, receptor | rs4994 | ADRB3: Trp64Arg | A/A |
| antipsychotic | Olanzapine | Schizophrenia more likely to improve | Low | 18320559 | DRD3 | dopamine receptor D3 | rs6280 | DRD3: SER9GLY | T/T |
| antipsychotic | Olanzapine | More likely to gain weight | Low | 19193342 | GNB3 | guanine nucleotide binding protein (G protein), beta polypeptide 3 | rs5443 | GNB3: 825C>T | C/T |
| antipsychotic | Olanzapine | More likely to gain weight | Low | 19193342 | HTR2A | 5-hydroxytryptamine (serotonin) receptor 2A | rs6313 | HTR2A: T102C | A/A |
| antipsychotic | Olanzapine | More likely to gain weight | Low | 19193342 | HTR2C | 5-hydroxytryptamine (serotonin) receptor 2C | rs6318 | HTR2C: Cys23Ser | C/C |

SUPPLEMENTAL TABLE 3c-continued

Pharmacogenotnic effects that are mixed and hard to integrate.

| Drug Class | Drug | Summary | Level of Evidence | PMID | Gene | Gene Name | rsID | Variant common name | Patient Genotype |
|---|---|---|---|---|---|---|---|---|---|
| antipsychotic | Olanzapine | More likely to gain weight | Low | 19434072 | HTR2C | 5-hydroxytryptamine (serotonin) receptor 2C | rs3813929 | HTR2C: −759C/T | C/C |
| antipsychotic | Olanzapine | Less likely to gain weight | Low | 19434072 | HTR2C | 5-hydroxytryptamine (serotonin) receptor 2C | rs518147 | HTR2C: −697G/C | C/C |
| antipsychotic | Risperidone | May not respond well | Low | 16604300 | RGS4 | regulator of G-protein signaling 4 | rs951439 | | C/C |
| antipsychotic | Risperidone | May not respond well | Low | 19451915 | COMT | catechol-O-methyltransferase | rs165599 | | A/A |
| antipsychotic | Risperidone | May respond well | Low | 18855532 | DRD2 | dopamine receptor D2 | rs1799978 | DRD2: −241A>G | T/T |
| antipsychotic | Risperidone | May respond well | Low | 19451915 | GRM3 | glutamate receptor, metabotropic 3 | rs724226 | | A/G |
| antipsychotic | Risperidone | May not respond well | Low | 18204343 | RGS4 | regulator of G-protein signaling 4 | rs10917670 | | C/C |
| antipsychotic | Risperidone | May not respond well | Low | 18204343 | RGS4 | regulator of G-protein signaling 4 | rs2661319 | | C/C |

What is claimed is:

1. A method for computation of the integrated genetic and environmental health risk of an individual, the method comprising:
    (a) analyzing genome sequence information from an individual for genetic risk of disease;
    (b) inputting data from the genetic risk analysis to an etiology integration engine;
    (c) determining etiological connections between diseases for which the individual has been determined to have a genetic risk;
    (d) making etiological connections between said diseases and environmental factors that are disease risk modifiers;
    wherein steps (a)-(d) are embodied as a program of instructions executable by computer and performed by means of software components loaded into the computer; and providing said individual with an assessment of integrated genetic and environmental health risks.

2. The method of claim 1, further providing said individual with a graphic output display of relationships between components.

3. The method of claim 1, further providing said individual with a personalized guide for prevention and/or treatment of the risks identified.

4. The method of claim 1, wherein the genome sequence information comprises the total sequence of an individual genome.

5. The method of claim 1, wherein the genome sequence information comprises a dataset of at least $5 \times 10^5$ single nucleotide polymorphisms.

6. The method of claim 5, wherein the genome sequence information comprises a dataset of at least $10^6$ single nucleotide polymorphisms.

7. The method of claim 6, wherein the genome sequence information further comprises a dataset of copy number variations in the individual genome.

8. The method of claim 5, wherein the genome sequence information is analyzed for variants in coding and non-coding regions for (i) variants associated with genes for Mendelian disease; (ii) novel mutations; (iii) variants known to modulate response to pharmacotherapy; and (iv) single nucleotide polymorphisms previously associated with complex disease.

9. The method of claim 8, wherein the analysis for variants compares variants to validated reference SNPs.

10. The method of claim 9, wherein the analysis for novel mutations comprises analysis with one or more of a "Sorting Intolerant from Tolerant" (SIFT) algorithm; a "Polymorphism Phenotyping"; a query for rare coding variants; and analysis for coding region variants that produce premature stop codons or read-throughs in existing stop codons.

11. The method of claim 10, wherein the analysis of SNPs for variants provides a disease association for which a likelihood ratio of disease risk is calculated.

12. The method of claim 11, wherein a pre-test probability for each disease is calculated.

13. The method of claim 12, wherein said pre-test probability is translated into pre-test odds, multiplied by the cumulative LR to get post-test odds, and then converted to a post-test probability calculation.

14. The method of claim 1, wherein gene-environment interaction with said diseases identified as a risk for said individual are determined.

15. A computer system configured for computation of the integrated genetic and environmental health risk of an individual, in a method comprising:
    (a) analyzing genome sequence information from an individual for genetic risk of disease;
    (b) inputting data from the genetic risk analysis to an etiology integration engine;
    (c) determining etiological connections between diseases for which the individual has been determined to have a genetic risk;
    (d) making etiological connections between said diseases and environmental factors that are disease risk modifiers; wherein steps (a)-(d) are embodied as a program of instructions executable by the computer and performed by means of software components loaded into the computer.

16. The computer system of claim 15, wherein said system comprises a database of the integrated genetic and environmental health risk of the individual.

* * * * *